(12) United States Patent
Lo et al.

(10) Patent No.: US 11,819,392 B2
(45) Date of Patent: *Nov. 21, 2023

(54) SYSTEM OF PANTILINERS AND MENSTRUAL PADS

(71) Applicant: Small Healthy Environment Limited, Hong Kong (HK)

(72) Inventors: Kam Fai Lo, Hong Kong (HK); Pak Yin Lo, Hong Kong (HK)

(73) Assignee: Small Healthy Environment Limited, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,787

(22) Filed: Feb. 3, 2023

(65) Prior Publication Data

US 2023/0181390 A1   Jun. 15, 2023

Related U.S. Application Data

(63) Continuation of application No. 16/600,744, filed on Nov. 8, 2019, now Pat. No. 11,596,559.

(51) Int. Cl.
*A61F 13/511* (2006.01)
*B32B 7/12* (2006.01)
(Continued)

(52) U.S. Cl.
CPC ...... *A61F 13/51121* (2013.01); *A61F 13/472* (2013.01); *A61F 13/55145* (2013.01);
(Continued)

(58) Field of Classification Search
CPC ........ A61F 13/47; A61F 13/472; A61F 13/51; A61F 13/53; A61F 13/511; A61F 13/514; A61F 13/551; A61F 13/56
See application file for complete search history.

(56) References Cited

U.S. PATENT DOCUMENTS 6,591,142 B1   7/2003   Dea
7,144,391 B1   12/2006  Kreutz et al.
(Continued)

FOREIGN PATENT DOCUMENTS

CN   201260741 Y   6/2009
CN   201304037 Y   9/2009
(Continued)

OTHER PUBLICATIONS

English Translation of Abstract of Chinese Patent Publication CN201260741 (Chinese Patent ZL 200820188997.8), Lao, J. "Feminine sanitary napkin," patent publication date Jun. 24, 2009.
(Continued)

*Primary Examiner* — Michele Kidwell
(74) *Attorney, Agent, or Firm* — Harvest IP Law LLP

(57) ABSTRACT

A system of pantiliners and menstrual pads that can be used to alleviate undesirable conditions associated with dysmenorrhea or other physiological conditions is provided. The pantiliners of the invention include a top layer of composite material, a ventilation layer, and a bottom layer of breathable material. The menstrual pads of the invention include a top layer of composite material, an air-laid layer, a layer of super adsorbent polymer inside the air-laid layer, a ventilation layer, and a bottom layer of breathable material. The present system of pantiliners and menstrual pads is helpful in providing a decrease of pain and other unwanted symptoms during a menstrual cycle. In another advantage, the right placement guide and the left placement guide are provided to assist in placing the menstrual pads of the invention accurately in relation to the undergarment of the user.

11 Claims, 9 Drawing Sheets

(51) Int. Cl.

| | |
|---|---|
| *B32B 5/02* | (2006.01) |
| *B32B 27/12* | (2006.01) |
| *B32B 27/32* | (2006.01) |
| *B32B 5/16* | (2006.01) |
| *A61F 13/56* | (2006.01) |
| *A61F 13/472* | (2006.01) |
| *B32B 5/26* | (2006.01) |
| *A61F 13/51* | (2006.01) |
| *A61F 13/47* | (2006.01) |
| *A61F 13/514* | (2006.01) |
| *A61F 13/551* | (2006.01) |

(52) U.S. Cl.
CPC ...... *A61F 13/5611* (2013.01); *A61F 13/5616* (2013.01); *B32B 5/022* (2013.01); *B32B 5/16* (2013.01); *B32B 5/26* (2013.01); *B32B 7/12* (2013.01); *B32B 27/12* (2013.01); *B32B 27/32* (2013.01); *A61F 2013/4708* (2013.01); *A61F 2013/51028* (2013.01); *A61F 2013/51078* (2013.01); *A61F 2013/51447* (2013.01); *B32B 2262/0253* (2013.01); *B32B 2262/067* (2013.01); *B32B 2262/103* (2013.01); *B32B 2262/12* (2013.01); *B32B 2307/724* (2013.01); *B32B 2307/726* (2013.01); *B32B 2555/02* (2013.01)

(56) References Cited

U.S. PATENT DOCUMENTS

| | | | |
|---|---|---|---|
| 7,754,345 B2 | 7/2010 | Tsai | |
| 8,961,483 B2 | 2/2015 | Shimizu et al. | |
| 9,433,542 B2 | 9/2016 | Kato et al. | |
| 9,655,791 B2 | 5/2017 | Rawat et al. | |
| 9,655,792 B2 | 5/2017 | Woo et al. | |
| 11,596,559 B2 * | 3/2023 | Lo | A61F 13/51121 |
| 2005/0261653 A1 | 11/2005 | Digiacomantonio et al. | |
| 2015/0283000 A1 | 10/2015 | Faulks et al. | |

FOREIGN PATENT DOCUMENTS

| | | |
|---|---|---|
| CN | 201494758 U | 6/2010 |
| CN | 201755286 U | 3/2011 |
| CN | 203133861 U | 8/2013 |
| CN | 208372027 U | 1/2019 |
| CN | 209377901 U | 9/2019 |
| WO | 2017209076 A | 12/2017 |
| WO | 2019061267 A1 | 4/2019 |

OTHER PUBLICATIONS

English Translation of Abstract of Chinese Patent Publication CN201755286 (Chinese Patent ZL 201020229032.6), Lao, J. "Novel sanitary towel," patent publication date Mar. 9, 2011.

Lee C. H. et al., "A multicenter, randomized, double-blind, placebo-controlled trial evaluating the efficacy and safety of a far infrared-emitting sericite belt in patients with primary dysmenorrhea," Complementary Therapies in Medicine (2011), 19, 187-193 (Jul. 16, 2011).

Liau, B.-Y et al. "Inhibitory Effects of Far-Infrared Ray-Emitting Belts on Primary Dysmenorrhea," Hindawi Publication Corporation, International Journal of Photoenergy, vol. 2012, Article ID 238468, 6 pages (Jun. 5, 2012).

Vatansever, F. et al. "Far infrared radiation (FIR): its biological effects and medical applications," Photonics Lasers Med. Nov. 1, 2012, 4:255-266.

Health Gate Anion Sanitary Napkins, Internet Article https://healthgate.me/anion-sanitary-napkins/.

Taiwan Intellectual Property Office, Office Action of Corresponding Taiwanese Patent Application Serial No. 109138835, dated May 28, 2021.

English Translation of Search Report in Office Action of Corresponding Taiwanese Patent Application Serial No. 109138835, dated May 28, 2021.

English Translation of Abstract of Chinese Patent Publication CN209377901 (U), Lin, D., Sep. 13, 2019.

English Translation of Abstract of Chinese Patent Publication CN203133861 (U), Jiang, S. et al., Aug. 14, 2013.

English Translation of Abstract of Chinese Patent Publication CN201494758 (U), Liu, P., Jun. 2, 2010.

English Translation of Abstract of Chinese Patent Publication CN201304037 (Y), Lao, J., Sep. 9, 2009.

English Translation of Abstract of Chinese Patent Publication CN208372027 (U), Li, S., Jan. 15, 2019.

Chinese National Intellectual Property Administration, Office Action of Corresponding Chinese Patent Application Serial No. 202080083023.7, dated Oct. 20, 2022.

English Translation of Office Action of Corresponding Chinese Patent Application Serial No. 202080083023.7, dated Oct. 20, 2022.

Chinese National Intellectual Property Administration, Second Office Action of Corresponding Chinese Patent Application Serial No. 202080083023.7, dated Apr. 29, 2023.

English Translation of Second Office Action of Corresponding Chinese Patent Application Serial No. 202080083023.7, dated Apr. 29, 2023.

English Translation of Current Claims referred to by Second Office Action of Corresponding Chinese Patent Application Serial No. 202080083023.7, dated Apr. 29, 2023.

* cited by examiner

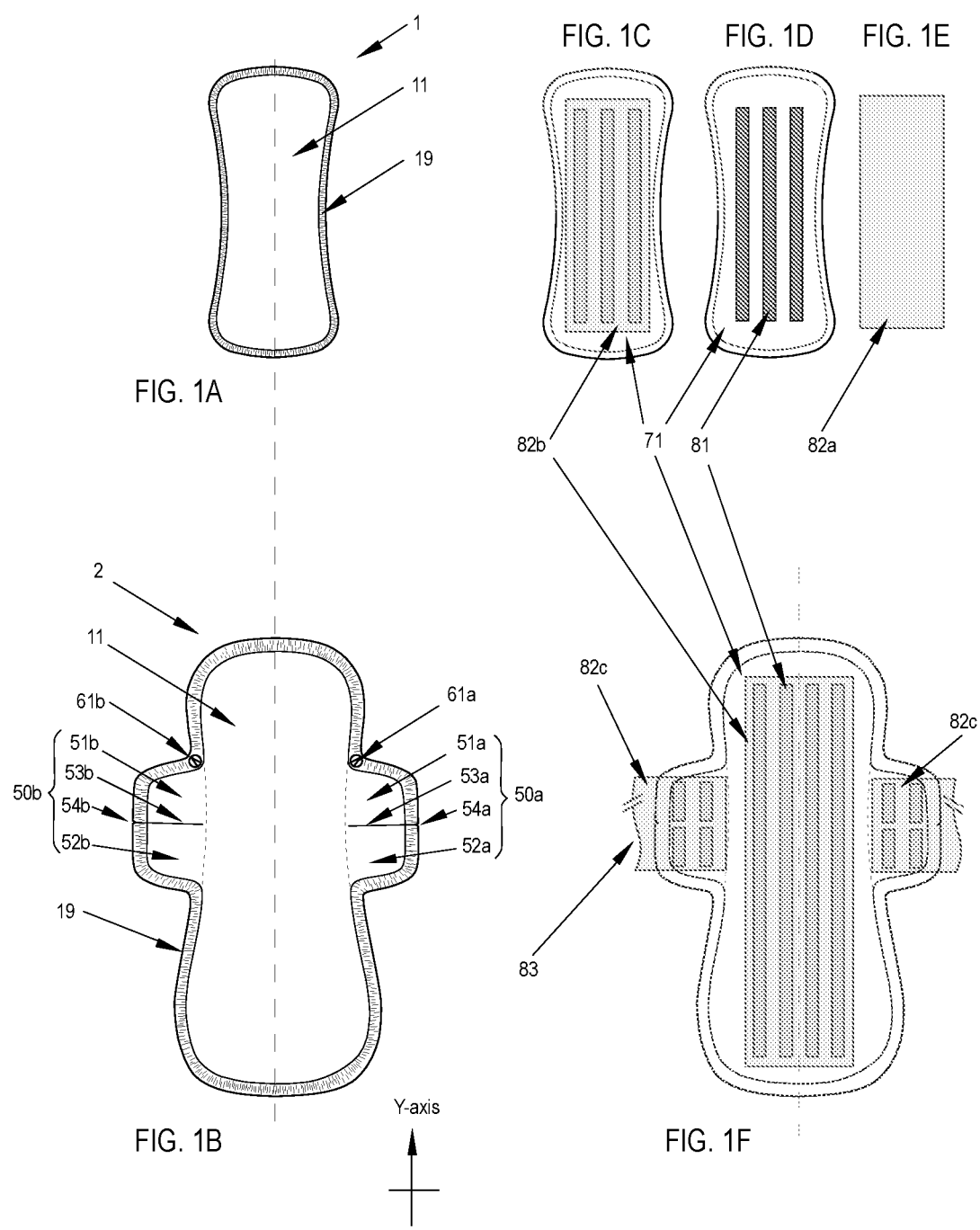

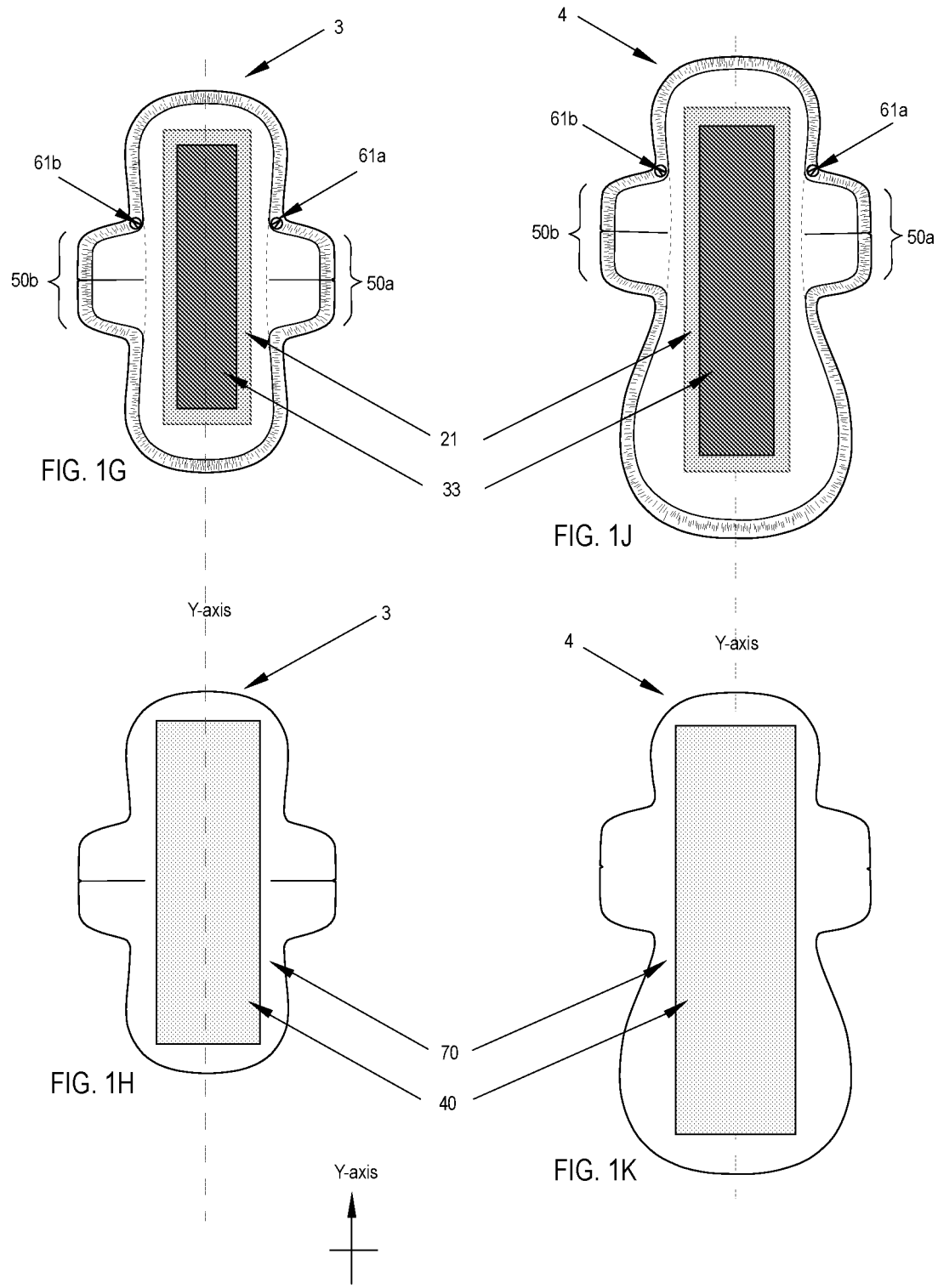

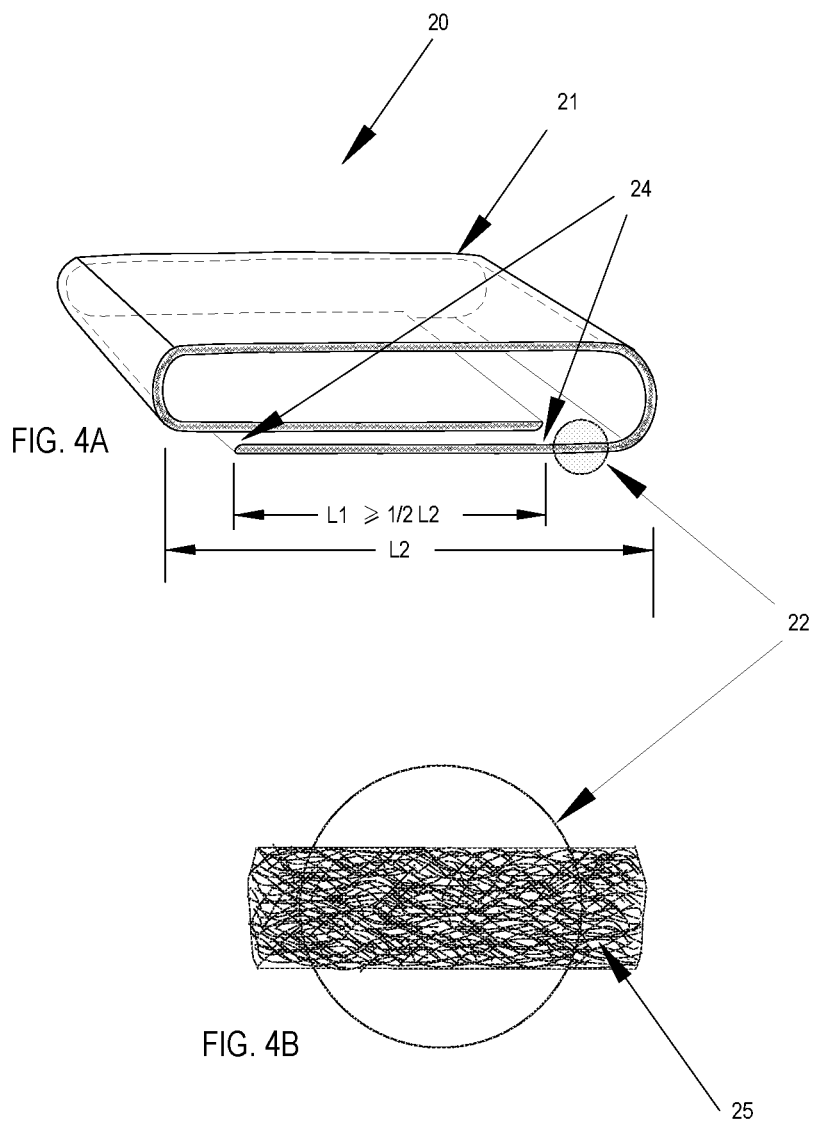

SYSTEM OF PANTILINERS AND MENSTRUAL PADS

CROSS REFERENCE TO RELATED APPLICATION

This application is a Continuation Application to U.S. application Ser. No. 16/600,744, filed on Nov. 8, 2019, now U.S. Pat. No. 11,596,559, issued on Mar. 7, 2023. The entire teaching of the above application is incorporated herein by reference.

FIELD

This application is directed to a system of pantiliners and menstrual pads that can be used to alleviate undesirable conditions associated with dysmenorrhea. By including a top layer of composite material that includes a body heat-loss decelerating and bacteria repelling material and a ventilation layer, the system of pantiliners and menstrual pads of the invention are able to bring about a decrease of number of days of cramp, and a decrease of pain during menstrual cycle.

BACKGROUND

Menstrual pads, or female sanitary napkins, are common consumer products that females use to take care of menstrual blood during their menstrual cycle. To achieve the primary function of absorbing and retaining the menstrual blood, most menstrual pads focus on using materials that are suitable as absorbents.

The Chinese utility model patent ZL 200820188997.8 (the '997 Patent) (Chinese Publication CN201260741) describes the use of nanoparticles as part of menstrual pads to stabilize the normal body temperature as a way to modify and decrease pain sensation during the menstrual period. On the other hand, the Chinese utility model patent ZL 201020229032.6 (the '032 Patent) (Chinese Publication CN201755286) describes the use of materials that can allow the ventilation of moisture and warm air as part of menstrual pads. However, menstrual pads according to these two Chinese documents (the '997 and '032 Patents) do not satisfy female consumers because: (a) they are not effective in diminishing the sensation of pain, and (b) any imprecise placement of the menstrual pad often would lead to leakage and falling off.

The Health Gate pantiliners and menstrual pads (https://healthgate.me/anion-sanitary-napkins/) are supposed to inhibit reproduction of anaerobic bacteria, improve microcirculation, increase the growth of bio-enzyme, regulate acidic secretions in the vaginal and improve women's self-protection and disease prevention ability. In addition, strontium ferrite is also added in the anion chip, which is bio-magnetic and activates the human bio-current, preventing various diseases and vaginal itching. But the Health Gate article does not provide scientific reasoning behind these biological effects. The Health Gate products also use water-absorbing particles that are fully wrapped by strictly sterilized, and dust-free paper. However, the Health Gate products do not disclose much detail on how the anion layer and the water-absorbing components are constructed. Furthermore, the Health Gate products do not suggest how to deal with leakage that a user would encounter.

Technological advances have provided new techniques for delivering far infrared radiation (FIR) to the human body. Specialty lamps and saunas, delivering pure FIR radiation, have become safe, effective, and widely used sources to generate therapeutic effects. Fibers impregnated with FIR emitting ceramic nanoparticles or coated with nano Zn/ZnO particles by the method of physical vapor deposition (PVD), are also found to be effective to alleviate muscle and joint pains.

Far infrared radiation has been reported to exhibit many biological effects by Vatansever et al. (Photonics Laser Med. 2012, 4, 225-266). The Vatansever report refers to another study using far infrared radiation emitting sericite belt to treat primary dysmenorrhea was carried out by C. H. Lee et al. (Complementary Therapies in Medicine 2011, 19, 187-193). It was found that the level of pain among the group of patients wearing the sericite belt was reduced more significantly than the patients wearing the placebo. However, no major difference was observed regarding the number of patients needing analgesics. Because this study according to C. H. Lee et al. involves a belt with infrared emitting sericite, this approach of using an infrared emitting belt is not suitable for pantiliners and menstrual pads.

Another study of the inhibitory effects of the far infrared emitting belt on primary dysmenorrhea was reported by B. Y. Liau et al. (International J. Photoenergy, 2012, Article 238468). It was shown that such treatment led to increasing regional surface temperature and abdominal blood flow and, reducing the level of pain. However, in this study according to B. Y. Liau et al., the far infrared emitting belt requires preheating at 50° C. for 30 minutes, and thus would not be suitable for pantiliners and menstrual pads. Therefore, there is still a need to provide a system of pantiliners and menstrual pads that can provide alleviation of painful sensation during the menstrual period.

Menstruation is the preparation for the next ovulation to take place. The menstrual cycle is an integral part of the physiology of females from puberty to menopause. Each menstrual cycle is about 28 days long, that includes:
  (a) a menstrual period (or menstrual phase) on about days 1-6,
  (b) a postmenstrual period (or postmenstrual phase) on about days 6-23, and
  (c) a premenstrual period (premenstrual phase) on about days 23-28.

Menstruation usually lasts for 3-6 days, with a flow volume of about 2 ml to 10 ml each for 12 to 20 times. The total flow volume should not exceed 80 ml to 100 ml for each menstruation. If fertilization fails to complete or does not occur, menstruation will resume after about 28 days from the first day of the previous menstrual cycle.

Premenstrual syndrome (PMS) is a combination of uncomfortable feelings that occur during days 23-28 of the menstrual cycle. PMS symptoms include:
  (a) physical symptoms such as fatigue, headache, weakness, weight gain, bloating, acne, fatigue, and skin problems; and
  (b) emotional symptoms such as mood swings, depression, anxiety, and trouble concentrating, irritability, and social withdrawal (https://my.clevelandclinic.org/health/articles/pms-and-pmdd).

Treatments of PMS are primarily using medication, exercising, or healthy diet to relieve the symptoms. However, there is no cure or prevention of PMS in today's medical service.

Primary dysmenorrhea and secondary dysmenorrhea are different types of pain being experienced during menstruation. According to the Cleveland Clinic, primary dysmenorrhea, or otherwise known as menstrual cramps, is related to the common and recurring pain that is not due to any disease (https://my.clevelandclinic.org/health/articles/dysmenorrhea). Menstrual cramps usually take place during days 1-3 of the menstrual cycle. To treat menstrual cramps in primary dysmenorrhea, taking pain-relieving medications such as ibuprofen, aspirin, or acetaminophen is common but not as effective as to other pains such as headaches, fever, etc. In addition, using heat pads (heat source facilitator), yoga (aerobic exercise), and massaging are the common approaches to relieve the pain of menstrual cramps.

Furthermore, primary dysmenorrhea, or menstrual cramps usually originate from pelvic organs, and the affected areas include the lower abdomen, spinal, back, and thigh. Menstrual cramps arise when the uterine muscle is tense and fatigue due to the slow restoration of adenosine triphosphate (ATP) for muscle movement. For muscles to relax, the myosin filaments are required to detach from the actin filaments, and such process requires ATP. Menstrual cramp is common if the body temperature is lower than 37° C. for a long time. According to traditional Chinese medicine (TCM) theory, when the body is cold or being affected by bad weather, primary dysmenorrhea is more likely to happen.

Secondary dysmenorrhea is related to a disorder of the woman's reproductive system such as endometriosis, adenomyosis, uterine fibroids, and infections. Muscle cramps encountered in secondary dysmenorrhea could be more sustained and intense. If secondary dysmenorrhea is suspected, immediate consultation with a medical professional and the performance of laboratory tests and pelvic examination are recommended because secondary dysmenorrhea can be very serious to body wellness.

According to a study of the prevalence of primary dysmenorrhea by Burnett et al. (J. Obstet. Gynecol. Can. 2005, 27, 765-70):

(a) About 9% encountered severe pain that results in loss of work or school;
(b) About 51% encountered moderate pain that results in limited activities, and
(c) About 40% will encounter normal pain that still allows freedom of movements Although the Burnett study was carried out in Canada, its results should be applicable to the United States, and to many other parts of the world. Therefore, it is reasonable to assume that about 60% of women of childbearing age experience cramps during their menstrual period.

Although cramps will usually subside as menstruation tapers off, analgesics and hormones cannot reduce pains effectively. However, if wrong and improper medications are used, then there could be more harm being done to the body. Therefore, it is the intention of the invention to achieve the goal of relieving painful conditions associated with menstrual cramps without the use of any medication.

SUMMARY

According to an embodiment of the invention, a pantiliner of the invention includes: (1) a top layer of composite material; (2) a ventilation layer; and (3) a bottom layer of breathable material. The top layer of composite material includes: (a) at least one layer of liquid permeable and breathable material, (b) at least one layer of structured glue, and (c) at least one layer of spun-bond polyethylene-polypropylene sheath-core bi-component fabric. The pantiliner is adapted and arranged to be useful during the premenstrual phase of a user of the pantiliner.

According to an embodiment of the pantiliner of the invention, regarding the top layer of composite material, the at least one layer of liquid permeable material comprises a polyethylene synthesized from non-woven fabric. The at least one layer of spun-bond polyethylene-polypropylene sheath-core bi-component fabric comprises fibers; and each fiber has a core part and a sheath part. The core part of the fiber comprises polypropylene as the primary material and nanosized metal compound as the secondary material. The sheath part of the fiber comprises polyethylene as the primary material and nanosized metal compound as the secondary material.

According to an embodiment of the pantiliner of the invention, the nanosized metal compound in the fibers is a far infrared emitting metal compound that is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, whereby the nanosized metal compound provides the user of the pantiliner: (a) relief of premenstrual syndrome by reducing body heat loss, and (b) reduced risk of infection by repelling bacteria that are mostly negatively charged.

According to an embodiment of the pantiliner of the invention, the ventilation layer is a non-woven sheet treated with polyethylene, and is sponge-like in structure having sufficient spaces for air ventilation, and the ventilation layer is rectangular in shape, having a width of 5.0 cm to 8.0 cm, and a length of 14.0 cm to 16.0 cm, whereby the ventilation layer provides the user of the pantiliner sufficient airflow by maintaining ventilation.

According to an embodiment, a menstrual pad of the invention includes: (1) a top layer of composite material having a skin contact surface; (2) an air-laid sheet; (3) a layer of super absorbent polymer inside the air-laid sheet; (4) a ventilation layer; and (5) a bottom layer of breathable material. The top layer of composite material comprises: (a) at least one layer of liquid permeable material, (b) at least one layer of structured glue, and (c) at least one layer of spun-bond polyethylene-polypropylene sheath-core bi-component fabric. The air-laid sheet is in the shape of an extendible tube that creates a wrap enclosure, and the menstrual pad is adapted and arranged to be useful during menstrual phase of a user of the menstrual pad.

According to an embodiment of the menstrual pad of the invention, regarding the top layer of composite material, the at least one layer of liquid permeable and breathable material comprises a polyethylene synthesized from non-woven fabric. The at least one layer of spun-bond polyethylene-polypropylene sheath-core bi-component fabric comprises fibers; and each fiber has a core part and a sheath part. The core part of the fiber comprises polypropylene as the primary material and nanosized metal compound as the secondary material. The sheath part of the fiber comprises polyethylene as the primary material and nanosized metal compound as the secondary material.

According to an embodiment of the menstrual pad of the invention, the nanosized metal compound in the fibers is a far infrared emitting metal compound that is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, whereby the nanosized metal compound provides the user of the menstrual pad: (a) relief of premenstrual syndrome by reducing body heat loss, and (b) reduced risk of infection by repelling bacteria that are mostly negatively charged.

According to an embodiment of the menstrual pad of the invention, with respect to the air-laid sheet, the extendible tube has a first edge and a second edge, the first edge and the second edge have an overlapping zone. The wrap enclosure has a lateral width, and the overlapping zone of the extendible tube has a length that is at least larger than one-half of the lateral width of the wrap enclosure. The air-laid sheet comprises polypropylene spun-bond fabric that is liquid permeable.

According to an embodiment of the pantiliner of the invention, the ventilation layer is a non-woven sheet treated with polyethylene, and is sponge-like in structure having sufficient spaces for air ventilation, whereby the ventilation layer provides the user of the menstrual pad sufficient airflow by maintaining ventilation.

According to an embodiment of the invention, the menstrual pad further includes: (6) a right placement mark on the right side of the menstrual pad, and a left placement mark on the left side of the menstrual pad. The right placement mark and the left placement mark each has a diameter of 3 mm to 8 mm. The right placement mark and the left placement mark each is printed or embossed on the skin contact surface.

According to an embodiment of the invention, the menstrual pad further includes: (7) a right split wing on the right side of the menstrual pad, and a left split wing on the left side of the menstrual pad. The right split wing can be split into an upper right split wing and a lower right split wing along a right split line. The left split wing can be split into an upper left split wing and a lower left split wing along a left split line.

According to an embodiment of a menstrual pad for use in daytime during the menstrual phase, the top layer of composite material and the bottom layer of breathable material each has an overall shape that is essentially identical with each other. The overall shape is dumbbell oval, having a minimal lateral width, a first maximal lateral width at an anterior end, a second maximal lateral width at a posterior end, and a longitudinal length. The minimal lateral width is 6.5 cm to 7.5 cm, the first maximal lateral width is 9.0 cm to 11.0 cm, the second maximal lateral width is 9.5 cm to 11.0 cm, and the longitudinal length is 23.0 cm to 26.0 cm.

According to an embodiment of a menstrual pad for use in nighttime during the menstrual phase, the top layer of composite material and the bottom layer of breathable material each has an overall shape that is essentially identical with each other. The overall shape is calabash oval, having a minimal lateral width, a first maximal lateral width at an anterior end, a second maximal lateral width at a posterior end, and a longitudinal length. The minimal lateral width is 7.5 cm to 9.5 cm, the first maximal lateral width is 9.5 cm to 11.0 cm, the second maximal lateral width is 14.0 cm to 16.0 cm, and the longitudinal length is 28.0 cm to 38.0 cm.

According to an embodiment of the invention, a method of using pantiliners and menstrual pads, includes the steps of: (a) using pantiliners during premenstrual phase, (b) using menstrual pads for use in daytime during daytime in menstrual phase, and (c) using menstrual pads for use in nighttime during nighttime in menstrual phase. The premenstrual phase can be 5-6 days, and the menstrual phase can be 4-6 days.

According to an embodiment of the invention, a method of determining primary dysmenorrhea in a user of a menstrual pad, includes the steps of: (a) observing a number of days of menstrual cramps without using the menstrual pad; (b) observing a number of days of menstrual cramps with using the menstrual pad; (c) subtracting the number of days of menstrual cramps with using the menstrual pad from the number of days of menstrual cramps without using the menstrual pad to obtain a shortened number of days of menstrual cramps, wherein the shortened number of days of menstrual crams is 1, 2, 3, 4, 5, or 6; (d) ranking effectiveness of the menstrual pad in shortening menstrual cramp as: (1) not effective, if the shortened number of days of menstrual cramp is 0; (2) moderately effective if the shortened number of day of menstrual cramp is 1; and (3) significantly effective if the shortened number of days of menstrual cramp is 2 or longer; (e) numerically describing a level of pain at the start of menstrual period with respect to a scale from 1 to 10, with "1" as the mildest level of pain, and "10" as the most severe level of pain; (f) numerically describing a level of pain at the end of menstrual period with respect to a scale from 1 to 10, with "1" as the mildest level of pain, and "10" as the most severe level of pain; (g) subtracting the level of pain at the end of menstrual period from the level of pain at the start of menstrual period to obtain a decrease level of pain, wherein the decrease level of pain is 0, 1, 2, 3, 4, 5, 6, 7, 8, 9, or 10; (h) ranking effectiveness of the menstrual pad in decreasing pain as: (1) not effective, if the decrease level of pain is 0; (2) moderately effective, if the decrease level of pain is 1, 2, or 3; and (3) significantly effective, if the decrease level of pain is 4 or more, and (i) determining the user of the menstrual pad as having primary dysmenorrhea: (1) if the effectiveness of the menstrual pad in shortening the number of days of menstrual cramp is moderately effective, or significantly effective, or (2) if the effectiveness of the menstrual pad in decreasing level of pain is moderately effective, or significantly effective.

According to an embodiment of the invention, a package of pantiliners and menstrual pads includes (1) a plurality of pantiliners; (2) a plurality of menstrual pads for use in daytime; and (3) a plurality of menstrual pads for use in nighttime. The plurality of pantiliners is 10 to 12 pieces, the plurality of menstrual pad for use in daytime is 15 to 18 pieces, and the plurality of menstrual pad for use in nighttime is 4 to 6 pieces.

BRIEF DESCRIPTION OF THE DRAWINGS

FIG. 1A is a top view of a pantiliner (1) of the invention.

FIG. 1B is a top view of a menstrual pad (2) of the invention.

FIG. 1C is a bottom view of a pantiliner (1) with release paper covering the surface glues on the exterior face of the pantiliner.

FIG. 1D is a bottom view of the pantiliner (1) with glue strips printed on the exterior face without the attachment of release paper.

FIG. 1E is a stand-alone release paper being taken out from the exterior face of the pantiliner (1).

FIG. 1F is a bottom view of the menstrual pad (2) with release paper covering the surface glues on the exterior of the menstrual pad.

FIG. 1G is a top view of a daytime menstrual pad (2) with an illustration of the position of the absorption body and the two placement marks.

FIG. 1H is a top view of a daytime menstrual pad (2) with an illustration of the position of the ventilation layer.

FIG. 1J is a top view of a nighttime menstrual pad (2) with an illustration of the positions of the absorption body and the two placement marks.

FIG. 1K is a top view of a nighttime menstrual pad (2) with an illustration of the position of the ventilation layer

FIG. 4A is a perspective view of an air-laid sheet in the shape of a wrap-enclosure of the menstrual pad (2).

FIG. 4B is a cross-section view of an air-laid sheet for the menstrual pad (2).

DETAILED DESCRIPTION OF THE EMBODIMENTS

Figure 2A:
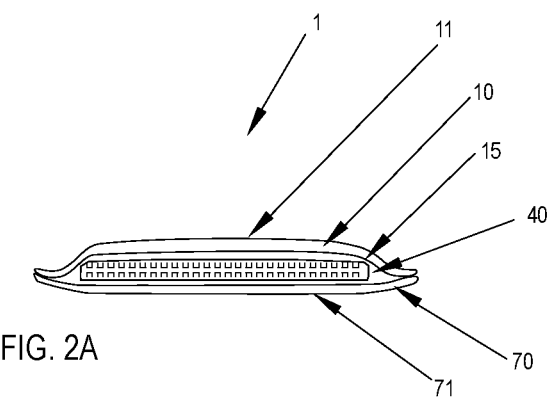
FIG. 2A is a cross-section view of the pantiliner (1) of the invention.

The invention uses a System of Pantiliners and Menstrual Pads that include a top layer of composite material that consists of a heat-loss decelerating, bacteria repelling and magnetic lines material, and a ventilation layer. As shown below in Example 1 and Table 2, by using pantiliners and menstrual pads according to the invention, users experience a reduced level of pain in menstrual cramps: (a) for some users, their level of pain changes from severe to moderate; (b) for some users, their level of pain changes from moderate to mild, and (c) for some users, their level of pain changes from mild to minimal.

This invention uses a heat-loss decelerating and bacteria repelling layer that contains far infrared radiation as well as negative ion emitting materials. It is generally believed that: (a) heat energy is transferred from the human body to the far infrared radiation emitting materials, and (b) heat energy is transferred from the far infrared radiation emitting materials back to the surface of the human body. As a result, in the presence or close proximity of the far infrared radiation emitting materials, heat loss from the body is minimized or decelerated. Thus, the consumption of ATP to keep the body warm is reduced, resulting in an abundance level of ATP. A higher level of ATP is beneficial because ATP also contributes to the relaxation of muscle by its binding to the myosin fibers and the detachment from the actin filaments. And also, it is generally believed that negative ion can give rise a bacteria-free environment as over 99.5% of bacteria carries negative charges in a warm and wet environment. This invention also uses a ventilation layer that can greatly reduce heat and moisture around so that fresh and clean air with ambient temperature around that further ensures user comfortability.

This invention is about delivering an effective solution to help alleviate premenstrual symptom PMS and primary dysmenorrhea without the addition of any additives including drugs, herbals, fragrances or chemicals. Although this invention cannot treat pains due to secondary dysmenorrhea, it can be used as a tester to decide whether seeking immediate medical treatments by gynecologist when appropriates.

On the other hand, this invention enables the ownership of a SMALL HEALTH ENVIRONMENT for childbearing age women attributing to (a) up-keeping the temperature of the uterus constant at 37° C., (b) maintaining surface temperature same as the ambient temperature, and (c) providing and maintaining a ventilated and sanitized surrounding.

The following listing provides numbers that corresponds to various parts in the drawings.

1 Feminine pantiliner article
2 Feminine menstrual pad article
3 Daytime menstrual pad article
4 Nighttime menstrual pad article
10 Top layer of composite material (or composite top sheet)
11 Skin contact surface (exterior surface of top-sheet)
12 Liquid permeable material made of polyethylene PE perforated spun-bond fabric for liquid acquisition
13 Structured glue
14 PE/PP mixed with nanosized metal compound sheath-core bicomponent for liquid acquisition and distribution
15 The back surface of top sheet
16 Core material by PP as the primary material
17 Selected nanosized metal compounds evenly distributed amongst the sheath-core fiber of the second layer of the top-sheet
18 Sheath (casing) material by PE as the secondary material
19 Embossment Strip along the edge of the pad
20 Air-laid sheet
21 Air-laid sheet in the shape of an extendable tube/wrap-enclosure
22 Cross section view of an air-laid sheet
23 An expanded/swollen wrap enclosure
24 The two opening edges of the overlapping area of the wrap-enclosure
25 Fabric texture of the air-laid sheet (liquid permeability spun-bond PP)
30 Absorption body
31 Super Absorbent Polymer (SAP) granule
32 Very thin wood-dust pulp
33 SAP-sheet (SAPs being laminated in between two thin wood-dust pulp)
34 Swollen SAP
40 Ventilation layer
41 Fabric texture of ventilation layer (high-loft with ample spaces for air ventilation)
50a Right split-wing (side-sheet)

50b Left split-wing (side-sheet)
51a Upper right split-wing
51b Upper left split-wing
52a Lower right split-wing
52b Lower left split-wing
53a Split cut line (right)
53b Split cut line (left)
54a Opening cut point (right)
54b Opening cut point (left)
55a Turn-over line (right)
55b Turn-over line (left)
56a Turn over (upper right) split-wing
56b Turn over (upper left) split-wing
57a Turn over (lower right) split-wing
57b Turn over (lower left) split-wing
58a Turn over V-shape split-wing (right)
58b Turn over V-shape split-wing (left)
60 Placement Guide System
61a Placement mark (right)
61b Placement mark (left)
62 Placement marks positioned at the intersection point
70 Bottom layer of breathable material (or back sheet of the pad)
71 The exterior face of the back sheet
80 Adhesives and release paper
81 Glue for the surface material
82a Release paper (stand-alone)
82b Release paper attached to surface glue strips over the back sheet of the pad
82c Release paper attached to surface glue strips over the back of the side wings
83 A tear-off line of the release paper covering the two side wings
90 Feminine Panty
91 Panty bridge
92a Right panty hole
92b Left panty hole
93a Right edge around right panty hole
93b Left edge around left panty hole According to FIG. 1A, which is a top view, a pantiliner article (1) includes a skin contact surface (11) and an embossment strip (19) along the perimeter of the pantiliner.

According to FIG. 1B, which is a top view, a day-use or night-use menstrual pad article (2) includes a skin contact surface (11), an embossment strip (19) along the perimeter of the menstrual pad, a pair of placement marks (61a, 61b), a pair of symmetric side-sheets or wings (50a, 50b), a pair of opening cut points (54a, 54b), a pair of split lines (53a, 53b) dividing the side-sheet into two smaller wings (51a, 52a, 51b, 52b).

According to FIG. 1C, which is a bottom view of the pantiliner (1), a release paper (82b) covers the surface of a plurality of glue strips (81) on the exterior face (71) of the pantiliner (1).

According to FIG. 1D, which is a bottom view of the pantiliner (1), the plurality of glue strips (81) is printed on the exterior face (71) of the pantiliner (1).

According to FIG. 1E, which is a top view, is a stand-alone release paper (82a) being detached from the back of the pantiliner (1).

According to FIG. 1F, which is a bottom view of the menstrual pad (2), a release paper (82b) covers the surface of a plurality of glue strips (81) on the exterior face (71) of the menstrual pad (2) and another two smaller release papers (82c) covering the surface glues (81) on the exterior face (71) of the two wings (50a, 50b), a tear-off line (83) to show these two smaller release papers should be in one piece before it is torn off and turned over as shown.

According to FIG. 1G, which is a top view of a daytime menstrual pad (3), the relative dimensions and the positions of both the air-laid sheet (21) and the SAP sheet (33) are illustrated.

According to FIG. 1H, which is a bottom view of the daytime menstrual pad (3), the relative dimensions and the position of the ventilation layer (40) on top of the back sheet or the bottom layer (70) are illustrated.

According to FIG. 1J, which is a top view of the nighttime menstrual pad (4), the relative dimensions and the positions of both the air-laid sheet (21) and the SAP sheet (33) are illustrated.

According to FIG. 1K, which is a bottom view of the nighttime menstrual pad (4), the relative dimensions and the position of the ventilation layer (40) on top of the back sheet or the bottom layer (70) are illustrated.

According to FIG. 2A, which is a cross-section view, the pantiliner (1) includes a top layer of composite material (or a composite top sheet) (10), a ventilation layer (40) and a bottom layer of breathable material (or breathable back sheet) (70). The composite top sheet (10) has a skin contact surface or an exterior surface (11), and a back surface or an interior surface (15). The back sheet (70) has an exterior face (71).

Figure 2B:
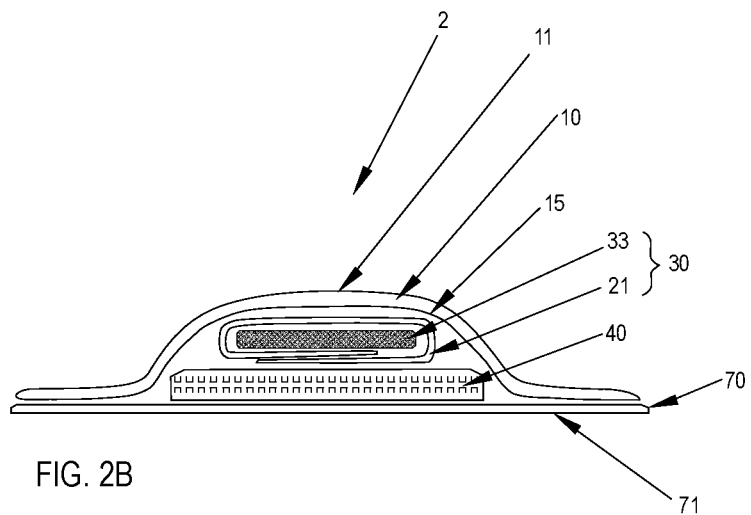
FIG. 2B is a cross-section view of the menstrual pad (2) of the invention.

According to FIG. 2B, which is a cross-section view, the menstrual pad (2) includes a composite top-sheet (10), an air-laid sheet in the shape of open edges wrap enclosure (21) embedded with a SAP-sheet (33), a ventilation layer (40) and a breathable back sheet (70). The composite top sheet (10) has a skin contact surface (11), and a back surface or an interior surface (15). The back sheet (70) has an exterior face (71).

Figures 3A, 3B, 3C, 3D, 3E:
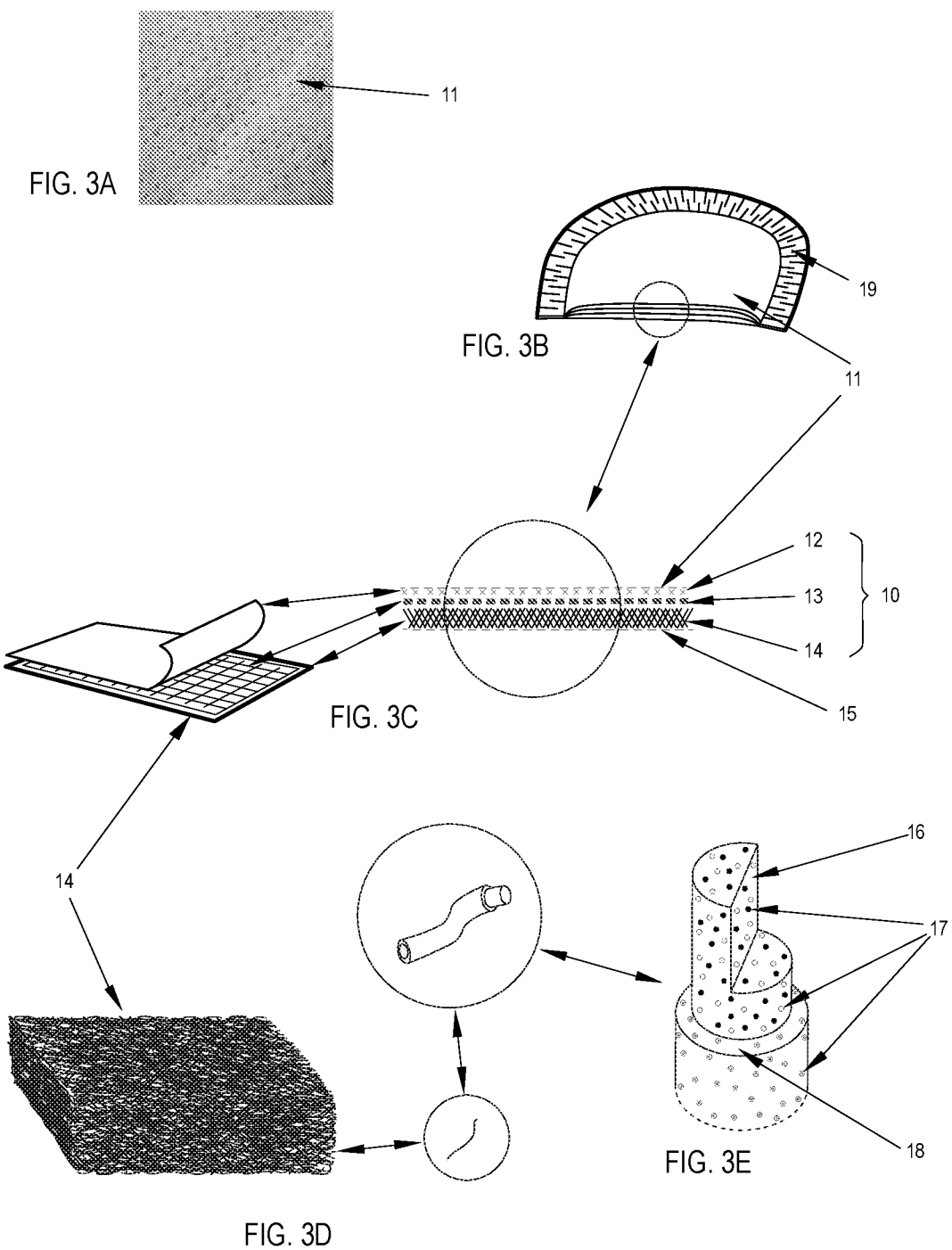
FIG. 3A is a top view of the skin contact surface of the top-sheet.
FIG. 3B is a side view of the top-sheet in 3D.
FIG. 3C is an enlarged cross-section view of the top-sheet of composite material.
FIG. 3D is an illustration of the PE/PP mixed with nanosized metal compound sheath-core bicomponent fabric of the top-sheet, and its internal fabric structure.
FIG. 3E is a perspective view of the material used in the fiber in a spun-bond PE/PP sheath-core bicomponent fabric.

According to FIG. 3A, which is a top view of the composite top-sheet for both the pantiliner (1) and the menstrual pad (2), a perforated texture sheet as a skin contact surface (11) is illustrated.

According to FIG. 3B, which is a side view, the composite top sheet (10) for both the pantiliner (1) and the menstrual pad (2) includes a skin contact surface (11), and an embossment strip (19) along the perimeter of the composite top sheet.

According to FIG. 3C, which is a cross-section view, the composite top sheet (10) includes a skin contact surface (11), a layer of liquid permeable material (12), a thin and discrete layer of structured glue (13), a spun-bond PE/PP sheath-core bicomponent fabric (14) for liquid acquisition and distribution, and a back surface (15).

According to FIG. 3D, which is an illustration of the spun-bond PE/PP sheath-core bicomponent fabric (14) in which each fiber comprises a sheath-core structure.

According to FIG. 3E, which is a perspective view of the material used in the fiber in a spun-bond PE/PP sheath-core bicomponent fabric (14), the fiber includes Polypropylene PP (16) as primary material and nanosized metal compound (17) as secondary material at the core part of the fiber, and Polyethylene PE (18) as primary material and nanosized metal compound (17) as secondary material at the sheath or casing part of the fiber.

According to FIG. 4A, which is a perspective view, the air-laid sheet (20) of the menstrual pad (2) is in the shape of an extendable tube or called a wrap enclosure (21) that comprises the polypropylene (PP) spun-bond fabric (25). For the air-laid sheet to work properly, it requires that the distance (L1) between the two open ends (24) of the wrap enclosure (21) must be longer than half of the total width (L2) of the wrap enclosure. This is to provide sufficient rooms for the wrap enclosure to expand.

According to FIG. 4B, which is a cross-section view, an air-laid sheet (22) comprises PP spun-bond fabric (25) that is liquid permeable. It should be noted that the air-laid sheet functions as a filter such that swollen SAP granules can never get away due to the densely spun-bond texture of the fabric. This ensures that the design of the wrap enclosure with SAP-sheet gives no chance of seepage or leakage whatsoever.

Figure 5A:
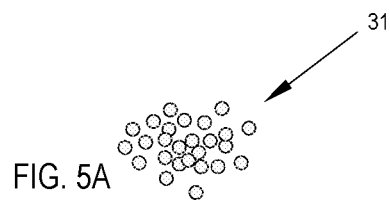
FIG. 5A is a top view of a group of dispersed Super Absorbent Polymer (SAP) granules.

According to FIG. 5A, which is a top view, a group of dispersed Super Absorbent Polymer granules (31) measures 0.03-0.05 mm as diameter when dry, and 1.1-1.8 mm as diameter when wet or swollen.

Figure 5B:
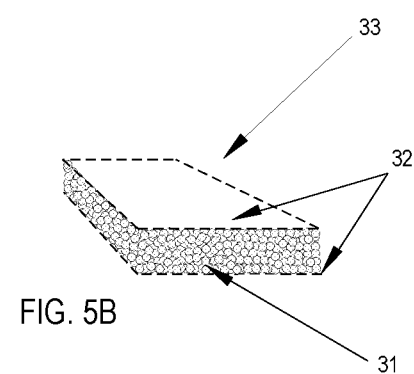
FIG. 5B is a side view of the SAP-sheet.

According to FIG. 5B, which is a perspective view, the SAP-sheet (33) comprises two pieces of thin wood dust pulp (32) for the exterior faces as top cover and back cover, and a layer of densely pressed SAP granules (31) being laminated between the two thin wood dust pulp (32).

Figure 5C:
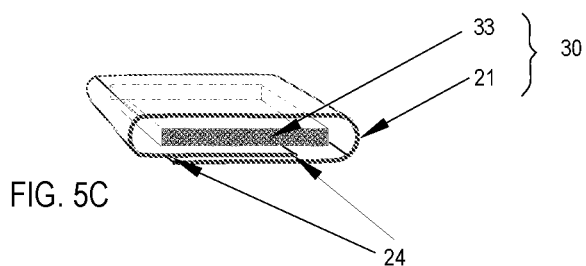
FIG. 5C is a perspective view of an absorption body comprises an air-laid wrap-enclosure together with a sacked-in SAP-sheet.

According to FIG. 5C, which is a perspective view, the absorption body (30) comprises an air-laid sheet in the shape of an extendable tube or a wrap enclosure (21), and a piece of SAP sheet (33) inside the wrap-enclosure (21). The open ends of the wrap enclosures are marked as (24).

Figure 5D:
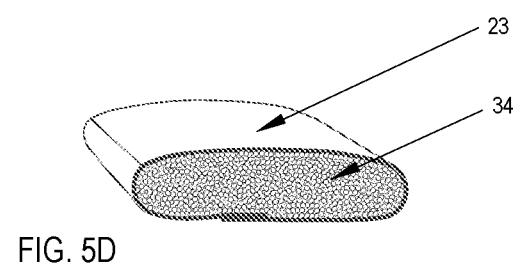
FIG. 5D is a side view of the swollen SAP in an expanded wrap enclosure.

According to FIG. 5D, which is a side view, a swollen absorption body (30) comprises an expanded wrap enclosure (23) and a collection of swollen SAP granules (34).

Figure 6A:
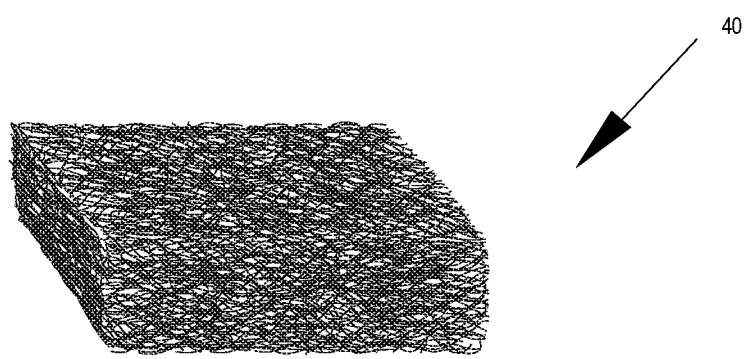
FIG. 6A is a side view of the ventilation layer by PP spun-bond for the pantiliner (1) and the pad (2).

According to FIG. 6A, which is a side view, the ventilation sheet (40) for both the pantiliner (1) and the menstrual pad (2) is illustrated as a fabric sheet comprising polyethylene PE spun-bond material.

Figure 6B:
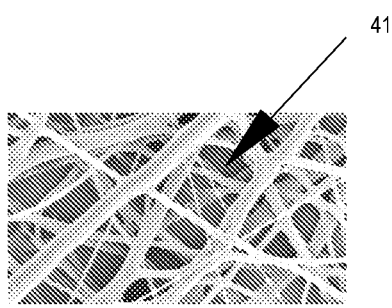
FIG. 6B is an internal view of the fabric of the ventilation layer for the pantiliner (1) and the pad (2).

According to FIG. 6B, which is an enlarged view of the internal structure of the ventilation layer (40), fabric structure (41) that is high-loft with ample spaces for air ventilation is shown.

Figure 7A:
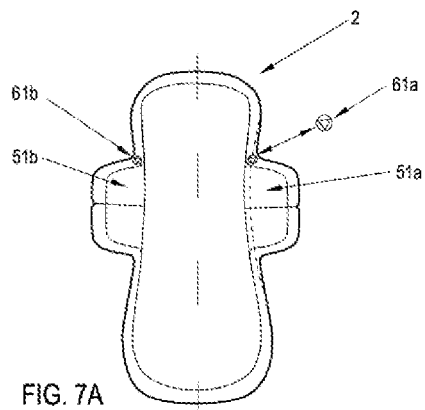
FIG. 7A is a top view of the placement mark on the top sheet of a menstrual pad (2).

According to FIG. 7A, which is a top view, the placement guide system (60) on the top sheet of the menstrual pad (2) comprises a pair of placement marks or guides (61a, 61b) being printed or embossed on the two anterior corners adjacent to the left upper wing (51b) and the right upper wing (51a). Both the right placement mark (61a) and the left placement mark 61b) are an identification mark that can be any kind of symbol, for example, ⊙, ❖, ✚, ★, ✈, ✜, or a company logo with diameter 3-7 mm.

Figure 7B:
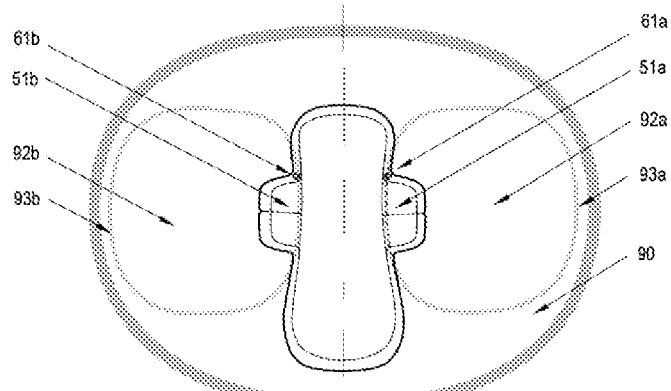
FIG. 7B is a top view of an illustration of the mechanism of placing a menstrual pad (2) onto a panty.

According to FIG. 7B, the steps of placing the menstrual pad (2) onto a panty (90) effectively are illustrated. By moving the pad (2) up and down along the y-axis until the right placement marks (61a) intersects with the right edge (93a) of the right panty holes (92a) while the left placement mark (61b) intersects with the left edge (93b) of the left panty hole (92b).

Figure 7C:
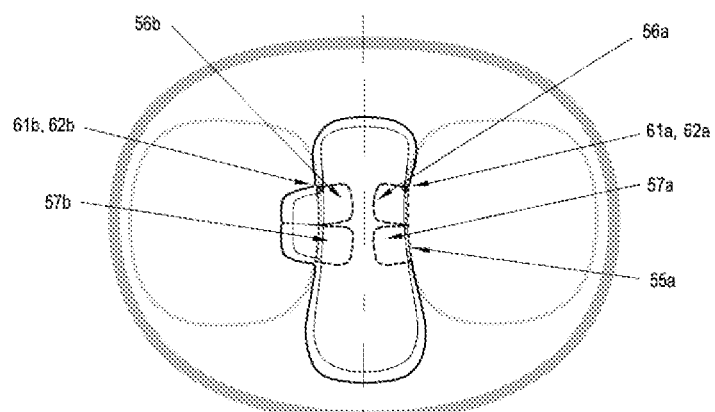
FIG. 7C is a top view of the correct placement position of the pad (2) onto a panty.

According to FIG. 7C, the correct position of the menstrual pad (2) onto the panty (90) is illustrated. The right placement mark (61a) is positioned at the right intersection point (62a), while the left placement mark (61b) is positioned at the left intersection point (62b). Upon locating the pad (2) at the correct position, the pad (2) can be attached on the top of the bridge (the center part) inside of the panty by folding the upper-right turn over split wing (56a) and the lower-right turn over split wing (57a) to the panty. Likewise, the upper-left turn over split wing (56b) and the lower-left turn over split wing (57b) should be folded to the panty.

Figure 8A:
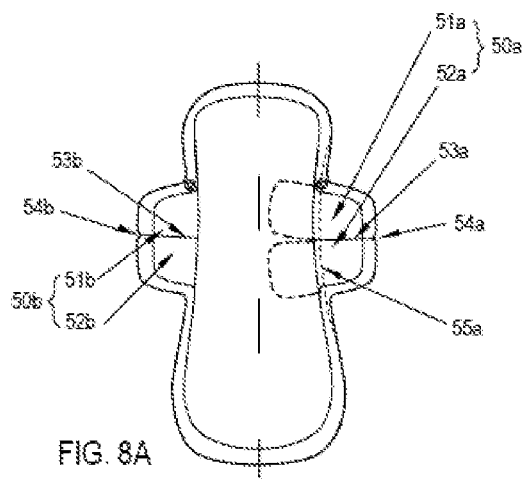
FIG. 8A is a top view of the split-wing of the menstrual pad (2)

According to FIG. 8A, which is a top view, the right split-wing (50a) and the left split-wing (50b) for the menstrual pad (2) comprise a pair of line-open-cut points (54a, 54b) at the middle edge of the side-sheets (50a, 50b), a pair of cut-out line (53a, 53b) at the middle of the side-sheets (50a, 50b), a pair of upper side-sheet (51a, 51b) and a pair of lower side-sheet (52a, 52b).

Figure 8B:
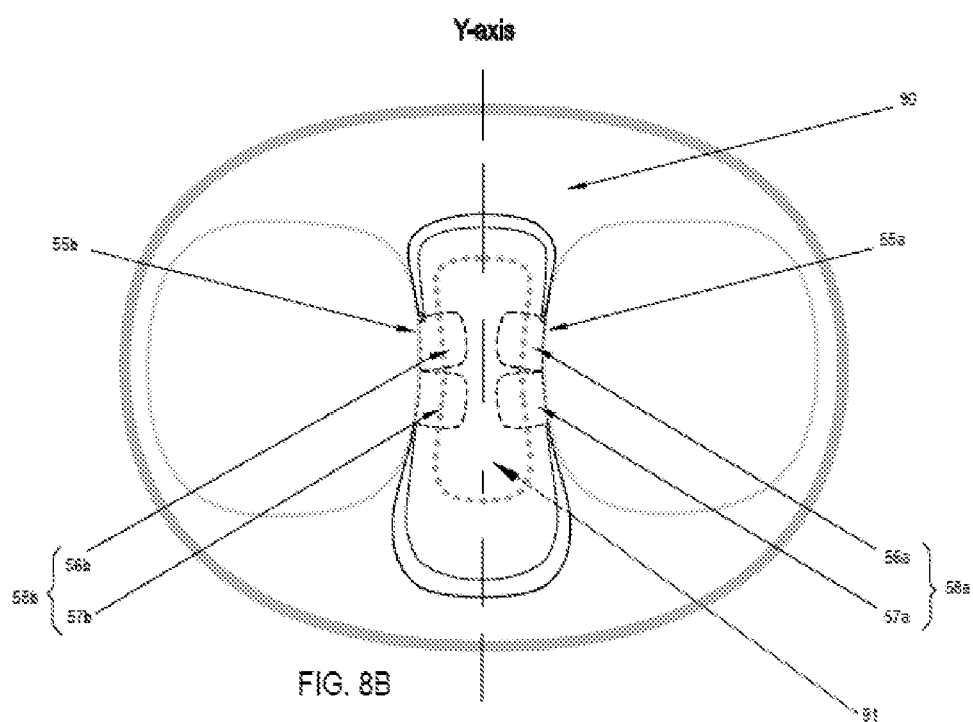
FIG. 8B is a top view of the menstrual pad (2) at its right position on a panty with its right wing being turned over attaching to the exterior face of the panty bridge.

According to FIG. 8B, which is a top view of a turn over split-wing of the menstrual pad (2), a turn over upper right side-sheet (56a), a turn over lower right side-sheet (57a), a perfect curvature line (55a) along the right inner edge of the panty, also an illustration of a V-shape of the turn over right side-sheet (58a).

Pantiliners

According to an embodiment, a pantiliner of the invention includes: (1) a top layer of composite material; (2) a ventilation layer; and (3) a bottom layer of breathable material. The top layer of composite material includes: (a) at least one layer of liquid permeable material, (b) at least one layer of structured glue, and (c) at least one layer of spun-bond polyethylene-polypropylene sheath-core bi-component fabric. The pantiliner is adapted and arranged to be useful during the premenstrual phase of a user of the pantiliner.

Referring to FIG. 1A (top view), FIG. 1C (back-view), FIG. 1D (back-view) and FIG. 2A (cross-section view), the pantiliner (1) includes the following major components: a top layer of composite material (10); a ventilation layer (40); and a bottom layer (back-sheet) of breathable material (70).

According to an embodiment of the pantiliner of the invention, regarding the top layer of composite material, the at least one layer of liquid permeable material comprises a polyethylene synthesized from non-woven fabric. The at least one layer of spun-bond polyethylene-polypropylene sheath-core bi-component fabric comprises fibers; and each fiber has a core part and a sheath part. The core part of the fiber comprises polypropylene as the primary material and nanosized metal compound as the secondary material. The sheath part of the fiber comprises polyethylene as the primary material and nanosized metal compound as the secondary material.

The description of the top layer of composite material can be found in FIG. 2A (cross-section view), FIG. 3A (top view), FIG. 3B (side view), FIG. 3C (cross-section view and side-view), FIG. 3D (side view and enlargement-view), and FIG. 3E (perspective-view): showing the top layer of the composite material (10) comprising the skin contact surface (11), a body liquid permeable material (12) as first layer, comprises a polyethylene PE spun-bond fabric, a thin and discrete layer of structured glue (13), and a spun-bond polyethylene/polypropylene (PE/PP) sheath-core bicomponent fabric (14) as second layer, and the bottom surface of the top sheet (15).

According to an embodiment of the pantiliner of the invention, the nanosized metal compound in the second layer of the top sheet of the fiber is a far infrared emitting metal compound that is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate.

As a result, the nanosized metal compound provides the user of the pantiliner: (a) relief of premenstrual syndrome by reducing heat loss, and (b) reduced risk of infection by repelling bacterial that are mostly negatively charged.

Additional examples of far infrared radiation emitting metal compounds have been reported by J. Y. Dea (U.S. Pat. No. 6,591,142) and J. H. Tsai (U.S. Pat. No. 7,754,345).

Referring to the various parts in FIG. 3D a side view of the fiber structure of the second layer (14) of the top-sheet and an enlargement view of the fiber, and referring to the various parts in FIG. 3E, a further enlargement of the fiber structure, comprises selected nanosized metal compound (17) evenly distribute around the sheath-core of the PE/PP spun-bond fiber. The fabric so composited can generate far infrared (FIR) radiation, negative ions as well as weak magnetic lines.

Referring to FIG. 3E, the nanosized metal compound mixes with Polypropylene PP (16) to form the core part and mixes with polypropylene PE to form the sheath (casing) part (18). The intensity of the FIR radiation generated by the fiber material (14) is in the waveband range of (3-12 µm) that has been observed in both in vitro and in vivo studies, to stimulate cells and tissue, and is considered a promising treatment modality for certain medical conditions.

One advantage of using nanosized far infrared emitting compounds is the effect of heat loss reduction. The embodiment of the invention is not about providing a heat-releasing pad, but a system of pantiliners and menstrual pad that generate FIR radiation to reduce the rate of body heat loss at the FIR radiation skin surface.

Another advantage is that the nanosized metal compound used in the shield casing (18) is capable of delivering 350 to 530 numbers of negative ions (anion) per $cm^3$ per second statically. As over 99.5% of bacteria are carrying negative charges, releasing of static anion by the fiber (14) ensures there will not be any bacteria around the pantiliner (1) and the menstrual pad (2) because same electric charges repels each other.

The existence of magnetic lines here provides a simple means to identify the fabric is built with the FIR and anion releasing properties by a handy magnetic reader. All physical properties of FIR radiation, negative ions as well as magnetic lines are made to meet the highest standard of safety requirement to our body.

According to an embodiment of the pantiliner of the invention, the ventilation layer is a non-woven sheet treated with polyethylene, is sponge-like in structure having sufficient spaces for air ventilation. The ventilation layer is rectangular in shape, having a width of 5.0 cm to 8.0 cm, and a length of 14.0 cm to 16.0 cm. As a result, the ventilation layer provides the user of the pantiliner sufficient airflow by maintaining ventilation.

Referring to FIG. 6A, a perspective-view of ventilation layer, and FIG. 68, an internal view of the fabric structure, the ventilation layer (40) comprises PE spun-bond fabric with high-loft (41) texture having sufficient spaces for air ventilation. See Table 1 as a summary of the dimensions of the ventilation layer in the pantiliner.

According to an embodiment of the pantiliner of the invention, the bottom layer of breathable material is poly-ethylene PE being extruded into very thin film with thickness of 0.02 mm to 0.05 mm with breathable holes for air coming in and out but not possible for water or body liquid.

Referring to FIG. 1D, a back view of the back-sheet or bottom layer (70) of the pantiliner (1), and FIG. 2A, a cross-section view of the back sheet (70) of the pantiliner (1), comprises polyethylene PE being extruded into a thickness of 0.02 mm to 0.05 mm film with breathable holes for air coming in and out but not possible for water or body liquid.

According to an embodiment of the pantiliner of the invention, the top layer of composite material and the bottom layer of breathable material each has an overall shape that is essentially identical with each other. The overall shape is a dumbbell oval, having a minimal lateral width, a first maximal lateral width at an anterior end, a second maximal lateral width at a posterior end, and a longitudinal length.

The minimal lateral width is 5.0 cm to 6.0 cm, the first maximal lateral width is 6.0 cm to 8.0 cm, the second maximal lateral width is 6.0 cm to 8.0 cm, and the longitudinal length is 14.0 cm to 16.0 cm.

Referring to FIG. 1A, a top view of the pantiliner (1), in FIG. 2A a cross-section view of the pantiliner (1), and in FIG. 1D, a back view of the pantiliner (1), the top layer (10) and the bottom layer (70) each have an overall shape that is essentially identical with each other. See Table 1 as a summary of the overall dimensions of the pantiliner.

Menstrual Pads in General

According to an embodiment, a menstrual pad of the invention includes: (1) a top layer of composite material having a skin contact surface; (2) an air-laid sheet in the shape of a wrap-closure; (3) a layer of super absorbent polymer inside the air-laid wrap enclosure; (4) a ventilation layer; and (5) a bottom layer of breathable material.

The top layer of composite material comprises: (a) at least one layer of liquid permeable material, (b) at least one layer of structured glue, and (c) at least one layer of spun-bond polyethylene-polypropylene sheath-core bi-component fabric. The air-laid sheet is in the shape of an extendible tube that creates a wrap enclosure, and the menstrual pad is adapted and arranged to be useful during menstrual phase of a user of the menstrual pad.

TABLE 1

Dimensions of Different Components of Pantiliner, Daytime Menstrual Pad, and Nighttime Menstrual Pad

| Dimensions | Pantiliner | Daytime Menstrual Pad | Nighttime Menstrual Pad |
| --- | --- | --- | --- |
| Minimal Lateral Width of Top/Bottom Layers | 5.0 cm-6.0 cm | 6.5 cm-7.5 cm | 7.5 cm-9.5 cm |
| First Maximal Lateral Width of Top/Bottom Layers | 6.0 cm-8.0 cm | 9.0 cm-11.0 cm | 9.5 cm-11.5 cm |
| Second Maximal Lateral Width of Top/Bottom Layers | 6.0 cm-8.0 cm | 9.0 cm-11.0 cm | 14.0 cm-16.0 cm |
| Longitudinal Length of Top/Bottom Layers | 14.0 cm-16.0 cm | 23.0 cm-26.0 cm | 28.0 cm-38.0 cm |
| Width of Ventilation Layer | 5.0 cm-8.0 cm | 5.5 cm-6.5 cm | 7.0 cm-8.5 cm |
| Length of Ventilation Layer | 14.0 cm-16.0 cm | 20.0 cm-24.0 cm | 27.0 cm-35.0 cm |
| Width of Air-Laid Layer/Wrap Enclosure | N/A | 5.0 cm-6.0 cm | 6.5 cm-7.5 cm |
| Length of Air-Laid Layer/Wrap Enclosure | N/A | 19.0 cm-23.0 cm | 24.0 cm-32.0 cm |
| Width of SAP Sheet | N/A | 4.5 cm-5.5 cm | 5.5 cm-7.0 cm |
| Length of SAP Sheet | N/A | 15.0 cm-19.0 cm | 18.0 cm-28.0 cm |

Referring to FIG. 1B (top view), FIG. 1F (back-view) and FIG. 2B (cross-section view) of the menstrual pad (2)

includes the following major components: a top layer of composite material (10); an absorption body (30); a ventilation layer (40) and a bottom layer/back-sheet of breathable material (70).

According to an embodiment of the menstrual pad of the invention, regarding the top layer of composite material, the at least one layer of liquid permeable material comprises a polyethylene synthesized from non-woven fabric. The at least one layer of spun-bond polyethylene-polypropylene sheath-core bi-component fabric comprises fibers; and each fiber has a core part and a sheath part. The core part comprises polypropylene as the primary material and nanosized metal compound as the secondary material. The sheath part comprises polyethylene as the primary material and nanosized metal compound as the secondary material.

Similarly, the description of the top layer of composite material can be found in FIG. 2B (cross-section view), FIG. 3A (top view), FIG. 3B (side view), FIG. 3C (cross-section view and side view), FIG. 3D (side view and enlargement view), and FIG. 3E (perspective-view): showing the top layer of the composite material (10) comprising the skin contact surface (11), a body liquid permeable material (12) as first layer, comprises a polyethylene PE spun-bond fabric, a thin and discrete layer of structured glue (13), and a spun-bond polyethylene/polypropylene (PE/PP) sheath-core bicomponent fabric (14) as second layer, and the bottom surface of the top sheet (15).

According to an embodiment of the menstrual pad of the invention, the nanosized metal compound which is capable of releasing far-infrared radiation, bacteria repelling negative ions well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate.

As a result, the nanosized metal compound provides the user of the menstrual pad: (a) relief of premenstrual syndrome by reducing heat loss, and (b) reduced risk of infection by repelling bacterial that are mostly negatively charged.

Referring to the various parts in FIG. 3D a side view of the fiber structure of the second layer (14) of the top-sheet and an enlargement view of the fiber, and referring to the various parts in FIG. 3E, a further enlargement of the fiber structure, comprises selected nanosized metal compound (17) evenly distribute around the sheath-core of the PE/PP spun-bond fiber. The fabric so composited can generate far infrared (FIR) radiation, negative ions as well as weak magnetic lines.

Referring to FIG. 3E, the nanosized metal compound is mixed with Polypropylene PP (16) to form the core part, mixed with polypropylene PE to form the sheath (casing) part (18). The intensity of the FIR radiation generated by the fiber material (14) is in the waveband range of (3-12 μm) that has been observed in both in vitro and in vivo studies, to stimulate cells and tissue, and is considered a promising treatment modality for certain medical conditions.

One advantage of using nanosized far infrared emitting metal compounds is the effect of heat loss reduction. The embodiment of the invention is not about providing a heat-releasing pad, but a system of pantiliners and menstrual pad that generate FIR radiation to reduce the rate of body heat loss at the FIR radiation skin surface.

Another advantage is that the nanosized metal compound used in the shield casing (18) is capable of delivering 350 to 530 numbers of negative ions (anion) per cm$^3$ per second statically. Over 99.5% of bacteria are carrying negative charges, releasing of static anion by the fiber (14) ensures there will not be any bacteria around the pantiliner (1) and the menstrual pad (2) because same electric charges repels each other.

The existence of magnetic lines here provides a simple means to identify the fabric is built with the FIR and anion releasing properties by a handy magnetic reader. All physical properties of FIR radiation, negative ions as well as magnetic lines are made to meet the highest standard of safety requirement to our body.

According to an embodiment of the menstrual pad of the invention, the extendible tube has a first edge and a second edge, the first edge and the second edge have an overlapping zone. The wrap enclosure has a lateral width, and the overlapping zone of the extendible tube has a length that is at least larger than one-half of the lateral width of the wrap enclosure. The air-laid sheet comprises polypropylene spun-bond fabric that is liquid permeable.

Referring to FIG. 4A, a perspective view of the air-laid (21) which is in the shape of an extendible tube similar to a wrap-enclosure, and FIG. 5C, a perspective view of the absorption body (30) comprises a SAP-sheet (33) inside of the air-laid wrap-enclosure (21), and in FIG. SD, a side view of an expanded absorption body (34), it requires that the length between the two open ends (L1) of the wrap-enclosure (24), is greater than half of the total width (L2) of the wrap-enclosure in order to sustain an open-end closed chamber upon expansion.

According to an embodiment of the menstrual pad of the invention, the layer of super absorbent polymer or called SAP-sheet (33) comprises super absorbent polymer granules that are pressed between two thin wood dust pulps. The granules have a diameter of 0.03 mm to 0.05 mm when dry, and 1.1 mm to 1.8 mm when wet or swollen.

Referring to FIG. 4A, a side-view of the air-laid sheet in the shape of an extendable tube (21) and FIG. 48, a cross-section view of the air-laid sheet (20), comprises polypropylene PP spun-bond liquid permeable material that serves as a filter to stop dry SAPs or swollen SAPs passing through. It should be noted that at the two opening edges of the wrap-enclosure (24), there must be an overlapping area in between. This invention requires that the overlapping length (L1) is greater than half of the width of the tube (L2) of the wrap-enclosure, for purpose of allowing enough rooms for expansion upon absorption of body liquid. The minimum liquid volume absorbable of a daytime pad and a nighttime pad are 80 cc and 120 cc respectively that makes every shed a peace of mind without worries of seepages.

The Super Absorbent Polymer (SAP) granules (31), measures 0.03-0.05 mm and 1.1-1.8 mm as diameter in dry mode and wet swollen mode respectively. The polymeric absorbing material (31) that is substantially super body liquid absorbable, water-insoluble and naturally neutralized, weights 150 gsm (grams per square meter) to 200 gsm.

Referring to FIG. 5C, a perspective view of the absorption body (30) and FIG. 5D, a side view of an expanded absorption body (34), a group of fully saturated SAPs (34) expands the chamber inside of the wrap-enclosure (21) to become the expanded wrap-enclosure (23). When menstrual blood permeates through top-sheet (10) and air-laid (21), the SAPs (31) inside of the SAP-sheet (33) absorbs it in seconds and is swollen 80-100 times of its original size (34). As swollen SAP (34) takes more spaces inside the extendable tube, the air-laid (21) at that moment is functioned as a filter to prevent SAP (34) coming out from the wrap-enclosure (23). Besides, there has no glue in between the overlapping area of the air-laid (24) so that it can expand freely to give more rooms for expansion.

According to an embodiment of the menstrual pad of the invention, the ventilation layer is a non-woven sheet treated with polyethylene PE, is sponge-like in structure having sufficient spaces for air ventilation. As a result, the ventilation layer provides the user of the menstrual pad sufficient airflow by maintaining ventilation.

Referring to FIG. 6A, a perspective-view of ventilation layer, and FIG. 6B, an internal view of the fabric structure, the ventilation layer (40) comprises PE spun-bond fabric with high-loft (41) texture having sufficient spaces for air ventilation.

According to an embodiment of the menstrual pad of the invention, the bottom layer of breathable material is polyethylene PE being extruded to very thin film with thickness of 0.02 mm to 0.05 mm with breathable holes for air coming in and out but not possible for water or body liquid.

Referring to FIG. 1F, a back view of the back-sheet or bottom layer (70) of the menstrual pad (2), and in FIG. 2B, a cross-section view of the bottom layer (70) of the menstrual pad (2), comprises polyethylene PE being extruded into a thickness of 0.02 mm to 0.05 mm film with breathable holes for air coming in and out but not possible for water or body liquid.

According to an embodiment of the invention, the menstrual pad further includes a right placement mark on the right side of the menstrual pad, and a left placement mark on the left side of the menstrual pad. The right placement mark and the left placement mark each has a diameter of 3 mm to 8 mm. The right placement mark and the left placement mark each is printed or embossed on the skin contact surface.

Referring to FIG. 1B, a top view of the menstrual pad (2), there is a 3-5 mm embossment strip (19) along the perimeter of the exterior face, a pair of side-sheet (50a, 50b) are attached to the top layer (10), and the upper corner of the left wing (51b, 52b) has a placement mark (61b); and the upper corner of the right wing (51a, 52a) has a placement mark or guide (61a). Each of the left placement mark or guide (61b) and the right placement mark or guide 61a) is an identification mark that can be any kind of symbol, for example, ☉, ❖, ✚, ★, ✈, ✒, or company logo with diameter 3-8 mm being printed or embossed on the two anterior corner adjacent to the left wing and the right wing.

Also referring to FIG. 7A, a top view of the menstrual pad (2), in FIG. 7B illustrates a menstrual pad (2) that is about to land on a desirable position on a feminine panty (90), and in FIG. 7C illustrates a menstrual is placed on the right place on the panty. By moving the pad (2) up and down along the y-axis until the placement marks (61a, 61b) intersect (62) with both the edge (93) of the left and right panty holes (92a, 92b). Upon locating the pad (2) at the right position, then stick the pad (2) on the top of the bridge (the center part) inside of the panty.

According to an embodiment of the invention, the menstrual pad further includes a right split wing on the right side of the menstrual pad, and a left split wing on the left side of the menstrual pad. The right split wing can be split into an upper right split wing and a lower right split wing along a right split line. The left split wing can be split into an upper left split wing and a lower left split wing along a left split line.

Referring to FIG. 8A, a top view of the menstrual pad (2), has a pair of side-sheet (50a, 50b), each side-sheet is being cut into two smaller wings or split wings by a split line (53a, 53b) with 3.0-4.0 cm at the middle of the side-sheet (50a, 50b). This gives perfect contouring along the edge of the panty (55a, 55b) and also a strong stay V-shape (57a, 57b) sticking effect when turning over and attaching the four little wings (51a, 51b, 52a, 52b) at the exterior face of the bridge of the panty. This minimizes the chance of pad movement or falling off.

Menstrual Pads for Use in Daytime

According to an embodiment of a menstrual pad for use in daytime during the menstrual phase, the top layer of composite material and the bottom layer of breathable material each has an overall shape that is essentially identical with each other. The overall shape is dumbbell oval, having a minimal lateral width, a first maximal lateral width at an anterior end, a second maximal lateral width at a posterior end, and a longitudinal length. The minimal lateral width is 6.5 cm to 7.5 cm, the first maximal lateral width is 9.0 cm to 11.0 cm, the second maximal lateral width is 9.0 cm to 11.0 cm, and the longitudinal length is 23.0 cm to 26.0 cm.

Referring to FIG. 1G, a top view of the menstrual pad (2) for use in daytime during the menstrual cycle, and in FIG. 1H, a back view of the menstrual pad (2) for use in daytime during the menstrual cycle, the top layer (10) and the bottom layer (70) each has an overall shape that is essentially identical with each other. See Table 1 as a summary of the overall dimensions of the daytime menstrual pad.

According to an embodiment of a menstrual pad for use in daytime during the menstrual phase, the wrap enclosure is rectangular in shape, having a width of 5.0 cm to 6.0 cm, and a length of 19.0 cm to 23.0 cm. The layer of super absorbent polymer inside the wrap enclosure is rectangular in shape, having a width of 4.5 cm to 5.5 cm, and a length of 15.0 cm to 19.0 cm.

Referring to FIG. 16, an out-lined top-view of the daytime menstrual pad (3), and in FIG. 2B a cross-section view of a menstrual pad (2), illustrates the dimension and position of the air-laid (21) as well as the SAP-sheet (33) with respect to the top-sheet of the daytime menstrual pad (3). The shape of the air-laid (21) is rectangular, having a lateral width of 5.0 cm to 6.0 cm, and the longitudinal length is 19.0 cm to 23.0 cm. The shape of the SAP-sheet is rectangular, having a lateral width of 4.5 cm to 5.5 cm, and the longitudinal length is 15.0 cm to 19.0 cm. See Table 1 as a summary of the dimensions of the SAP sheet and the air-laid sheet of the daytime menstrual pad.

According to an embodiment of a menstrual pad for use in daytime during the menstrual phase, the ventilation layer is rectangular in shape, having a width of 5.5 cm to 6.5 cm, and a length of 20.0 cm to 24.0 cm.

Referring to FIG. 1H, an out-lined top-view of the daytime menstrual pad (3), and in FIG. 2B a cross-section view of a menstrual pad (2), illustrates the dimension and position of the ventilation layer (40) with respect to the back sheet of the daytime menstrual pad (3). See Table 1 as a summary of the dimensions of the ventilation layer of the daytime menstrual pad.

Menstrual Pads for Use in Nighttime

According to an embodiment of a menstrual pad for use in nighttime during the menstrual phase, the top layer of composite material and the bottom layer of breathable material each has an overall shape that is essentially identical with each other. The overall shape is calabash oval, having a minimal lateral width, a first maximal lateral width at an anterior end, a second maximal lateral width at a posterior end, and a longitudinal length. The minimal lateral width is 7.5 cm to 9.5 cm, the first maximal lateral width is 9.5 cm to 11.5 cm, the second maximal lateral width is 14.0 cm to 16.0 cm, and the longitudinal length is 28.0 cm to 38.0 cm.

Referring to FIG. 1J, a top view of the menstrual pad (2) for use in nighttime during the menstrual cycle, and in FIG. 1K, a back view of the menstrual pad (2) for use in nighttime during the menstrual cycle, the top layer (10) and the bottom layer (70) each has an overall shape that is essentially identical with each other. See Table 1 as a summary of the overall dimensions of the nighttime menstrual pad.

According to an embodiment of a menstrual pad for use in nighttime during the menstrual phase, the wrap enclosure is rectangular in shape, having a width of 6.5 cm to 7.5 cm, and a length of 24.0 cm to 32.0 cm. The layer of super absorbent polymer inside the wrap enclosure is rectangular in shape, having a width of 5.5 cm to 7.0 cm, and a length of 18.0 cm to 28.0 cm.

Referring to FIG. 1J, an out-lined top-view of the nighttime menstrual pad (4), and in FIG. 2B a cross-section view of a menstrual pad (2), illustrates the dimension and position of the air-laid (21) as well as the SAP-sheet (33) with respect to the top-sheet of the nighttime menstrual pad (4). The shape of the air-laid (21) is rectangular, having a lateral width of 6.5 cm to 7.5 cm, and the longitudinal length is 24.0 cm to 32.0 cm. The shape of the SAP-sheet is rectangular, having a lateral width of 5.5 cm to 7.0 cm, and the longitudinal length is 18.0 cm to 28.0 cm. See Table 1 as a summary of the dimensions of the SAP sheet and the air-laid sheet of the nighttime menstrual pad.

According to an embodiment of a menstrual pad for use in nighttime during the menstrual phase, the ventilation layer is rectangular in shape, having a width of 7.0 cm to 8.5 cm, and a length of 28.0 cm to 38.0 cm.

Referring to FIG. 1K, an out-lined top-view of the nighttime menstrual pad (4), and in FIG. 2B a cross-section view of a menstrual pad (2), illustrates the dimension and position of the ventilation layer (40) with respect to the back sheet of the nighttime menstrual pad (4). The shape of the ventilation layer (40) is rectangular, having a lateral width of 7.0 cm to 8.5 cm, and the longitudinal length is 27.0 cm to 35.0 cm. See Table 1 as a summary of the dimensions of the ventilation layer of the nighttime menstrual pad.

Using Pantiliners and Menstrual Pads

According to an embodiment of the invention, a method of using pantiliners and menstrual pads, includes the steps of: (a) using pantiliners according to claim 1 during premenstrual phase, (b) using menstrual pads for use in daytime according claim 16 during daytime in menstrual phase, and (c) using menstrual pads for use in nighttime according to claim 19 during nighttime in menstrual phase. The premenstrual phase can be 5-6 days, and the menstrual phase can be 4-6 days.

Determining Primary Dysmenorrhea

A method of determining primary dysmenorrhea in a user of a menstrual pad, includes the steps of:
(a) observing a number of days of menstrual cramps without using the menstrual pad;
(b) observing a number of days of menstrual cramps with using the menstrual pad;
(c) subtracting the number of days of menstrual cramps with using the menstrual pad from the number of days of menstrual cramps without using the menstrual pad to obtain a shortened number of days of menstrual cramps, wherein the shortened number of days of menstrual camps is 0, 1, 2, 3, 4, 5, or 6;
(d) ranking effectiveness of the menstrual pad in shortening menstrual cramp as:
  (1) not effective, if the shortened number of days of menstrual cramp is 0;
  (2) moderately effective, if the shortened number of days of menstrual cramp is 1; or
  (3) significantly effective, if the shortened number of days of menstrual cramp is 2 or longer;
(e) numerically describing a level of pain at the start of menstrual period with respect to a scale from 1 to 10, with "1" as the mildest level of pain, and "10" as the most severe level of pain;
(f) numerically describing a level of pain at the end of menstrual period with respect to a scale from 1 to 10, with "1" as the mildest level of pain, and "10" as the most severe level of pain;
(g) subtracting the level of pain at the end of menstrual period from the level of pain at the start of menstrual period to obtain a decrease level of pain, wherein the decrease level of pain is 0, 1, 2, 3, 4, 5, 6, 7, 8, 9, or 10; and
(h) ranking effectiveness of the menstrual pad in decreasing pain as:
  (1) not effective, if the decrease level of pain is 0;
  (2) not effective, if the decrease level of pain is 1, 2, or 3; or
  (3) significantly effective, if the decrease level of pain is 4 or more; and
(i) determining the user of the menstrual pad as having primary dysmenorrhea:
  (1) if the effectiveness of the menstrual pad in shortening the number of days of menstrual cramp is moderately effective, or significantly effective, or
  (2) if the effectiveness of the menstrual pad in decreasing the level of pain is moderately effective, or significantly effective.

In summary, for a user of menstrual pad having primary dysmenorrhea, the menstrual pad is considered to be effective in shortening the number of days of menstrual cramp if the menstrual pad can at least show "moderately effective," or "significantly effective" in shortening the number of days having menstrual cramps. Similarly, the menstrual pad is considered to be effective in decreasing pain if the menstrual pad can at least show moderately effect," or "significantly effective" in lowering the level of pain.

On the other hand, if the user of the menstrual pad does not experience any positive effect with regard to (a) shortening the number of days of menstrual cramp, or (b) decreasing the level of pain, then such user is likely to have secondary dysmenorrhea. Immediate medical diagnosis and treatment are recommended.

Referring to Tables 2, 3, and 4, the use of the menstrual pad system according to the invention is useful: (a) in shorting the number of days of menstrual cramps, and (b) in decreasing the level pain. Users with primary dysmenorrhea will experience moderate effectiveness or significant effectiveness in either: (a) shortening the number of days of cramps, or (b) decreasing the level of pain. The users are recommended to continue to use the menstrual pad system of the invention.

In contrast, users with secondary dysmenorrhea will experience no effectiveness in either (a) shortening the number of days of cramps, or (b) decreasing the level of pain. They are recommended to seek help from a medical professional as soon as possible.

A Package of Pantiliners and Menstrual Pads

According to an embodiment of the invention, a package of pantiliners and menstrual pads includes: (1) a plurality of pantiliners; (2) a plurality of menstrual pads for use in daytime; and (3) a plurality of menstrual pads for use in nighttime. The plurality of pantiliners is 10 to 12 pieces, the plurality of menstrual pad for use in daytime is 15 to 18 pieces, and the plurality of menstrual pad for use in nighttime is 4 to 6 pieces.

Preferably, the plurality of pantiliners is 12 pieces that will be sufficient for 6 days with 1 for daytime and 1 for nighttime; preferably the plurality of menstrual pad for use in daytime is 18 pieces; and preferably the plurality of menstrual pad for use in nighttime is 6 pieces.

Advantages of the Pantiliners and Menstrual Pads

In summary, the invention provides a number of advantages to the pantiliners and the menstrual pads:

(A) Heat loss reduction: The nanosized metal compounds in the top layer of composite material provide far infrared radiation (FIR) that contributes to reducing the loss of heat by the users. Many users experience less menstrual cramps and less pain.

(B) Antibacterial Effect: The nanosized metal compounds in the top layer of composite material deliver negative ions that are helpful in repelling bacteria because most bacteria carry negative charges.

(C) Liquid acquisition and distribution: The top layer of composite material having a layer of liquid permeable layer, a layer of structured glue, and a layer of spunbond polyethylene-polypropylene sheath-core bi-component fabric is beneficial because this top layer make the acquisition and distribution of blood fluid manageable.

(D) Efficient handling of swollen super absorbent polymer granules: Keeping super absorbent polymer granules inside an air-laid sheet that is in the shape of an extendible tube is very helpful because the extendible tube creates a wrap enclosure that can be expanded to efficiently hold the swollen granules inside the air-laid sheet.

(E) Placement Marks: The use of a pair of placement marks is advantageous because users can place the menstrual pads precisely, efficiently, and easily on the underpants and thus leakage is effectively avoided.

(F) Split Wings: The use of a pair of split wings that can in turn be split to become upper split wings and lower split wings is an effective way of securing the menstrual pads onto the underpants. As a result, the menstrual pad is firmly attached around the undergarment, and leakage is further avoided.

(G) Fresh air inside out: The use of a ventilation layer placing on top of the bottom layer ensures an effective means of securing a fully ventilated surrounding for ambient temperature and humidity around.

EXAMPLE

The following example is set forth so as to provide those of ordinary skill in the art with a complete disclosure and description of how to make and use the present invention. The example is not intended to limit the scope of what the inventors regard as their invention, nor are they intended to represent that the evaluation and testing described below are all or the only evaluation and testing performed.

Example 1

Effects of Using Menstrual Pads Before Menstrual Phase Begins

A group of 29 users, having an average age 36 and a range of age from 24 to 55, was asked to report the effects of using menstrual pads that are equipped with a body heat-loss decelerating layer (Table 2). Each user started using the menstrual pads before the menstrual phase began for a certain number of days (column 3).

The users reported the number of days of menstrual cramps without using menstrual pads (column 4), and the number of days of menstrual cramps using pads (column 5). The data was analyzed and categorized in the following way (column 6): (a) if there was no change, the data is categorized as "none"; (b) if there was shortening of the number of days of menstrual cramps by one day, the data is categorized "moderate"; and (c) if there was shortening of the number of days of menstrual cramps by at least two days, the data is categorized as "significant".

It can be observed that, with respect to the number of days experiencing menstrual cramps, 11 users showed no change of the number of days of cramp, 12 users showed "moderate" change, and 6 users showed "significant" change. Therefore, a combined 18 users out of 29 users showed that the use of a menstrual pad was effective in decreasing the number of days experiencing menstrual cramps.

The users also reported: (a) the level of pain at the start of period (column 7), with "1" as the mildest level of pain, and "10" as the most severe level of pain, and (b) the level of pain at the end of the period (column 8) with respect to a scale from 1 to 10, with "1" as the mildest level of pain, and "10" as the most severe level of pain. The data was analyzed and categorized in the following way (column 10): (a) if there was no change of the level of pain, the data is categorized as "none"; (b) if there was a decrease of pain by −1, −2, or −3, the data is categorized as moderate; and (c) if there was a decrease of pain by −4, −5, −6, or −7, the data is categorized as "significant".

It can be observed that, with respect to the level of pain, 3 users showed no change of the level of pain, 10 users showed "moderate" change, and 16 users showed "significant" change. Therefore, a combined 26 users out of 29 users showed that the use of pad was effective in decreasing the level of pain.

It should be noted that user #1 and user #10 of the menstrual pad do not experience any improvement in terms of (a) the shortening of the number of days of menstrual cramps, and (b) the decrease of level of pain from the start of the menstrual period to the end of the menstrual period. A possible explanation is that both of these users do not have primary dysmenorrhea. Instead, they likely have secondary dysmenorrhea, which is related to a disorder of the woman's reproductive system such as endometriosis, adenomyosis, uterine fibroids, and infections. These users should seek medical help as soon as possible.

TABLE 2

Effects of Using Menstrual Pads Before Menstrual Period

| User | Age | # Days of Using Pad Before Period | # Days of Cramps Without Using Pads | # Days of Cramps Using Pads | Effectiveness of Pads in Shortening # Days of Cramps | Level of Pain at Start of Period | Level of Pain at End of Period | Change of Level of Pain | Effectiveness of Pads in Relieving Pain |
|---|---|---|---|---|---|---|---|---|---|
| 1 | 34 | 7 | 3 | Entire Period | None | 7 | 8 | +1 | None |
| 2 | 33 | 7 | 2 | 2 | None | 9 | 5 | −4 | Significant |

TABLE 2-continued

Effects of Using Menstrual Pads Before Menstrual Period

| User | Age | # Days of Using Pad Before Period | # Days of Cramps Without Using Pads | # Days of Cramps Using Pads | Effectiveness of Pads in Shortening # Days of Cramps | Level of Pain at Start of Period | Level of Pain at End of Period | Change of Level of Pain | Effectiveness of Pads in Relieving Pain |
|---|---|---|---|---|---|---|---|---|---|
| 3 | 30 | 3 | 3 | 3 | None | 7 | 5 | −2 | Moderate |
| 4 | 38 | 4 | 3 | 2 | Moderate | 8 | 2 | −6 | Significant |
| 5 | 36 | 5 | 3 | 1 | Significant | 9 | 7 | −2 | Moderate |
| 6 | 46 | 10 | 2 | 0 | Significant | 7 | 0 | −7 | Significant |
| 7 | 33 | 7 | 3 | 1 | Significant | 8 | 3 | −5 | Significant |
| 8 | 33 | 2 | 3 | 2 | Moderate | 8 | 5 | −3 | Moderate |
| 9 | 45 | 7 | 3 | 2 | Moderate | 9 | 4 | −5 | Significant |
| 10 | 49 | 7 | 3 | 3 | None | 6 | 6 | 0 | None |
| 11 | 28 | 7 | 2 | Not Reported | None | 8 | 3 | −5 | Significant |
| 12 | 31 | 4 | 1 | 1 | None | 7 | 5 | −2 | Moderate |
| 13 | 33 | 10 | 2 | 1 | Moderate | 7 | 3 | −4 | Significant |
| 14 | 34 | 7 | 2 | 2 | None | 9 | 7 | −2 | Moderate |
| 15 | 35 | 7 | 2 | 2 | None | 9 | 3 | −6 | Significant |
| 16 | 49 | 2 | 5 | 2 | Significant | 10 | 4 | −6 | Significant |
| 17 | 24 | 7 | 3 | Not Reported | None | 7 | 3 | −4 | Moderate |
| 18 | 38 | 7 | 3 | 2 | Moderate | 10 | 8 | −2 | Moderate |
| 19 | 29 | 9 | 3 | 2 | Moderate | 9 | 3 | −6 | Significant |
| 20 | 33 | 7 | 3 | 2 | Moderate | 7 | 6 | −1 | Moderate |
| 21 | 24 | 7 | 3 | 1 | Significant | 9 | 2 | −7 | Significant |
| 22 | 39 | 7 | 2 | Entire Period | None | 10 | 3 | −7 | Significant |
| 23 | 38 | 7 | 3 | 2 | Moderate | 10 | 4 | −6 | Significant |
| 24 | 55 | 7 | 3 | 2 | Moderate | 6 | 1 | −5 | Significant |
| 25 | 33 | 7 | 3 | 1 | Significant | 8 | 2 | −6 | Significant |
| 26 | 47 | 7 | 3 | 2 | Moderate | 9 | 3 | −6 | Significant |
| 27 | 34 | 7 | 3 | 2 | Moderate | 8 | 5 | −3 | Moderate |
| 28 | 32 | 7 | 2 | 2 | None | 10 | 9 | −1 | Moderate |
| 29 | 28 | 7 | 2 | 1 | Moderate | 8 | 8 | 0 | None |

TABLE 3

Recommendation Based on Shortened Number of Days of Cramps

| Shortened Number of Days of Cramps After Using Pad System | Effectiveness | Recommendation |
|---|---|---|
| 0 | Not Effective | Cramps may be due to secondary dysmenorrhea; consult physician |
| 1 | Moderately Effective | Keep on using pad system |
| 2 | Significantly Effective | Keep on using pad system |

TABLE 4

Recommendation Based on Decrease Level of Pain

| Decreased Level of Pain After Using Pad System | Effectiveness | Recommendation |
|---|---|---|
| 0 | Not Effective | Cramps may be due to secondary dysmenorrhea; consult physician |
| 1, 2, or 3 | Moderately Effective | Keep on using pad system |
| 4, 5, 6, 7, 8, 9, or 10 | Significantly Effective | Keep on using pad system |

What is claimed is:

1. A menstrual pad for use in nighttime during the menstrual phase, comprising:
   a top layer of composite material having a skin contact surface;
   an air-laid sheet;
   a layer of super absorbent polymer inside the air-laid sheet;
   a ventilation layer; and
   a bottom layer of breathable material; wherein
   the top layer of composite material comprises:
      at least one layer of liquid permeable material,
      at least one layer of structured glue, and
      at least one layer of spun-bond polyethylene-polypropylene sheath-core bi-component fabric,
   the air-laid sheet is in shape of an extendible tube that creates a wrap enclosure, and the menstrual pad is adapted and arranged to be useful during menstrual phase of a user of the menstrual pad, wherein
   the at least one layer of liquid permeable material comprises a polyethylene synthesized from non-woven fabric, and
   the at least one layer of spun-bond polyethylene-polypropylene sheath-core bi-component fabric comprises fibers, each fiber has a core part and a sheath part, wherein
   the core part comprises polypropylene as the primary material, and nanosized metal compound as the secondary material, and
   the sheath part comprises polyethylene as the primary material, and nanosized metal compound as the secondary material, wherein
   the nanosized metal compound which is capable of releasing far-infrared emitting, bacteria repelling as well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate,
   whereby the nanosized metal compound provides the user of the menstrual pad: (a) relief of menstrual cramp by reducing heat loss, and (b) reduced risk of infection by repelling bacteria that are mostly negatively charged, wherein the top layer of composite material and the bottom layer of breathable material each has an overall shape that is essentially identical with each other, the overall shape is calabash oval, having a minimal lateral width, a first maximal lateral width at an anterior end, a second maximal lateral width at a posterior end, and a longitudinal length, wherein the minimal lateral width is 7.5 cm to 9.5 cm, the first maximal lateral width is 9.5 cm to 11.5 cm, the second maximal lateral width is 14.0 cm to 16.0 cm, and the longitudinal length is 28.0 cm to 38.0 cm.

2. The menstrual pad for use in nighttime according to claim 1, wherein the wrap enclosure is rectangular in shape, having a width of 6.5 cm to 7.5 cm, and a length of 24.0 cm to 32.0 cm, and the layer of super absorbent polymer inside the air-laid sheet is rectangular in shape, having a width of 5.5 cm to 7.0 cm, and a length of 18.0 cm to 28.0 cm.

3. The menstrual pad for use in nighttime according to claim 1, wherein the ventilation layer is rectangular in shape, having a width of 7.0 cm to 8.5 cm, and a length of 27.0 cm to 35.0 cm.

4. The menstrual pad according to claim 1, wherein the extendible tube has a first edge and a second edge, the first edge and the second edge have an overlapping zone, the wrap enclosure has a lateral width, and the overlapping zone of the extendible tube has a length that is at least larger than one-half of the lateral width of the wrap enclosure, and the air-laid sheet comprises polypropylene spun-bond fabric that is liquid permeable.

5. The menstrual pad according to claim 1, wherein the layer of super absorbent polymer comprises super absorbent polymer granules that are pressed between two thin wood dust pulp, and the granules have a diameter of 0.03 mm to 0.05 mm when dry, and 1.1 mm to 1.8 mm when wet or swollen.

6. The menstrual pad according to claim 1, wherein the ventilation layer is a non-woven sheet treated with polyethylene, is sponge-like in structure having sufficient spaces for air ventilation, whereby the ventilation layer provides the user of the menstrual pad sufficient airflow by maintaining ventilation.

7. The menstrual pad according to claim 1, wherein the bottom layer of breathable material is polyethylene PE being extruded to very thin film with thickness of 0.02 mm to 0.05 mm with breathable holes for air coming in and out but not possible for water or body liquid.

8. The menstrual pad according to claim 1, further comprising:

a right placement mark on the right side of the menstrual pad; and a left placement mark on the left side of the menstrual pad, wherein the right placement mark and the left placement mark each has a diameter of 3 mm to 8 mm, and the right placement mark and the left placement mark each is printed or embossed on the skin contact surface.

9. The menstrual pad according to claim 1, further comprising:

a right split wing on the right side of the menstrual pad; and a left split wring on the left side of the menstrual pad, wherein the right split wing can be split into an upper right split wing and a lower right split wing along a right split line, and the left split wing can be split into an upper left split wing and a lower left split wing along a left split line.

10. A method of using pantiliners and menstrual pads, comprising the steps of:

(a) using a pantiliner during premenstrual phase, the pantiliner comprises a top layer of composite material; a ventilation layer; and a bottom layer of breathable material, wherein the top layer of composite material comprises:

at least one layer of liquid permeable material, at least one layer of structured glue, and at least one layer of spun-bond polyethylene-polypropylene sheath-core bi-component fabric, wherein the at least one layer of liquid permeable material comprises a polyethylene synthesized from non-woven fabric, the at least one layer of spun-bond polyethylene-polypropylene sheath-core bi-component fabric comprises fibers, each fiber has a core part and a sheath part, the core part comprises polypropylene as the primary material and nanosized metal compound as the secondary material, and the sheath part comprises polyethylene as the primary material and nanosized metal compound as the secondary material, wherein the nanosized metal compound which is capable of releasing far-infrared emitting, bacteria repelling as well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, wherein the nanosized metal compound provides the user of the pantiliner: (a) relief of premenstrual syndrome by reducing heat loss, and (b) reduced risk of infection by repelling bacteria that are mostly negatively charged;

(b) using a menstrual pad for use in daytime during daytime in menstrual phase, wherein the menstrual pad for use in daytime comprises a top layer of composite material having a skin contact surface;

an air-laid sheet;

a layer of super absorbent polymer inside the air-laid sheet;

a ventilation layer; and a bottom layer of breathable material; wherein the top layer of composite material comprises:

at least one layer of liquid permeable material, at least one layer of structured glue, and at least one layer of spun-bond polyethylene-polypropylene sheath-core bi-component fabric, the air-laid sheet is in shape of an extendible tube that creates a wrap enclosure, and the menstrual pad is adapted and arranged to be useful during menstrual phase of a user of the menstrual pad, wherein the at least one layer of liquid permeable material comprises a polyethylene synthesized from non-woven fabric, and the at least one layer of spun-bond polyethylene-polypropylene sheath-core bi-component fabric comprises fibers, each fiber has a core part and a sheath part, wherein the core part comprises polypropylene as the primary material, and nanosized metal compound as the secondary material, and the sheath part comprises polyethylene as the primary material, and nanosized metal compound as the secondary material, wherein the nanosized metal compound which is capable of releasing far-infrared emitting, bacteria repelling as well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, wherein the top layer of composite material and the bottom layer of breathable material each has an overall shape that is essentially identical with each other, the overall shape is dumbbell oval, having a minimal lateral width, a first maximal lateral width at an anterior end, a second maximal lateral width at a posterior end, and a longitudinal length, wherein the minimal lateral width is 6.5 cm to 7.5 cm, the first maximal lateral width is 9.0 cm to 11.0 cm, the second maximal lateral width is 9.0 cm to 11.0 cm, and the longitudinal length is 23.0 cm to 26.0 cm (c) using a menstrual pad for use in nighttime according to claim 1 during nighttime in menstrual phase, wherein the premenstrual phase can be 5-6 days, and the menstrual phase can be 4-6 days.

11. A package of pantiliners and menstrual pads, comprising:

a plurality of pantiliners;

a plurality of menstrual pads for use in daytime; and a plurality of menstrual pads for use in nighttime, wherein (a) the pantiliner comprises a top layer of composite material; a ventilation layer; and a bottom layer of breathable material, wherein the top layer of composite material comprises:
  at least one layer of liquid permeable material,
  at least one layer of structured glue, and
  at least one layer of spun-bond polyethylene-polypropylene sheath-core bi-component fabric, wherein the at least one layer of liquid permeable material comprises a polyethylene synthesized from non-woven fabric, the at least one layer of spun-bond polyethylene-polypropylene sheath-core bi-component fabric comprises fibers, each fiber has a core part and a sheath part, the core part comprises polypropylene as the primary material and nanosized metal compound as the secondary material, and the sheath part comprises polyethylene as the primary material and nanosized metal compound as the secondary material, wherein the nanosized metal compound which is capable of releasing far-infrared emitting, bacteria repelling as well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, wherein the nanosized metal compound provides the user of the pantiliner: (a) relief of premenstrual syndrome by reducing heat loss, and (b) reduced risk of infection by repelling bacteria that are mostly negatively charged;

(b) the menstrual pad for use in daytime comprises a top layer of composite material having a skin contact surface;

an air-laid sheet;

a layer of super absorbent polymer inside the air-laid sheet;

a ventilation layer; and a bottom layer of breathable material; wherein the top layer of composite material comprises:
  at least one layer of liquid permeable material,
  at least one layer of structured glue, and
  at least one layer of spun-bond polyethylene-polypropylene sheath-core bi-component fabric, the air-laid sheet is in shape of an extendible tube that creates a wrap enclosure, and the menstrual pad is adapted and arranged to be useful during menstrual phase of a user of the menstrual pad, wherein the at least one layer of liquid permeable material comprises a polyethylene synthesized from non-woven fabric, and the at least one layer of spun-bond polyethylene-polypropylene sheath-core bi-component fabric comprises fibers, each fiber has a core part and a sheath part, wherein the core part comprises polypropylene as the primary material, and nanosized metal compound as the secondary material, and the sheath part comprises polyethylene as the primary material, and nanosized metal compound as the secondary material, wherein the nanosized metal compound which is capable of releasing far-infrared emitting, bacteria repelling as well as magnetic lines, is a member of the group consisting of aluminum oxide, aluminum silicate, calcium carbonate, iron oxide, magnesium oxide, nickel oxide, silicon carbide, silicon dioxide, tin dioxide, titanium dioxide, zinc oxide, zirconium carbide, zirconium dioxide, and zirconium silicate, wherein the top layer of composite material and the bottom layer of breathable material each has an overall shape that is essentially identical with each other, the overall shape is dumbbell oval, having a minimal lateral width, a first maximal lateral width at an anterior end, a second maximal lateral width at a posterior end, and a longitudinal length, wherein the minimal lateral width is 6.5 cm to 7.5 cm, the first maximal lateral width is 9.0 cm to 11.0 cm, the second maximal lateral width is 9.0 cm to 11.0 cm, and the longitudinal length is 23.0 cm to 26.0 cm, (c) the menstrual pad for use in nighttime is according to claim 1, the plurality of pantiliners is 10 to 12 pieces, the plurality of menstrual pad for use in daytime is 15 to 18 pieces, and the plurality of menstrual pad for use in nighttime is 4 to 6 pieces.

\* \* \* \* \*